US009353070B2

(12) United States Patent
Dochnahl et al.

(10) Patent No.: US 9,353,070 B2
(45) Date of Patent: May 31, 2016

(54) CARBAMAT-BENZOXAZINONES

(71) Applicant: BASF SE, Ludwigshafen (DE)

(72) Inventors: Maximilian Dochnahl, Munich (DE); Roland Goetz, Neulussheim (DE); Joachim Gebhardt, Wachenheim (DE); Uwe Josef Vogelbacher, Ludwigshafen (DE); Timo Frassetto, Mannheim (DE); Michael Rack, Eppelheim (DE); Volker Maywald, Ludwigshafen (DE); Bernd Wolf, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/421,348

(22) PCT Filed: Aug. 7, 2013

(86) PCT No.: PCT/EP2013/066562
§ 371 (c)(1),
(2) Date: Feb. 12, 2015

(87) PCT Pub. No.: WO2014/026893
PCT Pub. Date: Feb. 20, 2014

(65) Prior Publication Data
US 2015/0299148 A1  Oct. 22, 2015

Related U.S. Application Data

(60) Provisional application No. 61/684,161, filed on Aug. 17, 2012.

(30) Foreign Application Priority Data

Aug. 17, 2012  (EP) .................................... 12180824

(51) Int. Cl.
C07D 265/36  (2006.01)
C07D 413/04  (2006.01)

(52) U.S. Cl.
CPC ............ *C07D 265/36* (2013.01); *C07D 413/04* (2013.01)

(58) Field of Classification Search
CPC ...................................................... C07D 265/36
USPC ........................................................ 544/105
See application file for complete search history.

(56) References Cited

FOREIGN PATENT DOCUMENTS

| EP | 0 237 899 | 9/1987 |
|---|---|---|
| JP | 56-152448 | 11/1981 |
| JP | 58-52256 | 3/1983 |
| WO | WO 2006/060494 | 6/2006 |
| WO | WO 2006/129100 | 12/2006 |
| WO | WO 2010/145992 | 12/2010 |
| WO | WO 2011/057935 | 5/2011 |
| WO | WO 2013/024007 | 2/2013 |
| WO | WO 2013/092850 | 6/2013 |
| WO | WO 2013/092856 | 6/2013 |

OTHER PUBLICATIONS

Kirsanov, A.V., "Dimethylamides of alkoxydichloroacetic acids", Zhurnal obshchei khimii, Nauka, Moscow, Jan. 1, 1959, p. 100-1005, vol. 29.
Yagupolskii, L.M., "Reactions of (Aryloxy)-,(Arylthio)-, and (Arylsulfonyl)- Difluoroacetic esters with ammonia and amines", Journal of General Chemistry USSR, Consultants Bureau, New York, NY, 1969, p. 1711-1714, vol. 39, No. 8.
Cai et al., "Dication $C(R^1)$-$N(R^2)_2$ Synthons and their use in the Synthesis of Formamidines, Amidines, and alpha-Aminonitriles", Tetrahedron, vol. 56, No. 42, Oct. 13, 2000, pp. 8253-8262.
Johnson et al., "Nonenzymatic Conversion of Penicillins to 6-Aminopenicillanic Acid", The Journal of Organic Chemistry, vol. 31, No. 8, Aug. 1, 1966, pp. 2560-2564.
Reany et al., "A model system using modulation of lanthanide luminescence to signal Znin competitive aqueous media", Journal of the Chemical Society, Perkins Transactions 2, No. 9, Sep. 1, 2000, pp. 1819-1831.
Techer et al., "Amides tertiaires de l'acide oxo-3-dihydro-2,3 benzoxazine-1,4 carboxylique-2", Comptes Rendus Des Seances De L'Academie Des Sciences, Serie C:Sciences Chimiques, vol. 270, Jan. 1, 1970, pp. 107-110.
Office Action dated Jul. 29, 2015 in U.S. Appl. No. 14/365,822.
Office Action dated Aug. 4, 2015 in U.S. Appl. No. 14/365,829.
European Search Report dated Oct. 24, 2012, from European Patent Application No. 12180824.
International Preliminary Report on Patentability dated Feb. 17, 2015, prepared in International Application No. PCT/EP2013/066562.
International Search Report dated Sep. 6, 2013, prepared in International Application No. PCT/EP2013/066562.
Etienne, Andre et al. "Isocyanurates de diallyle-1.3 et d'aryle-5", Chemistry Organique, Sep. 1975, p. 275-278, vol. 281.

*Primary Examiner* — Kahsay Habte
(74) *Attorney, Agent, or Firm* — Brinks Gilson & Lione

(57) ABSTRACT

The present invention relates to carbamat-benzoxazinones of formula (I), wherein the variables are defined according to the description,
as well as to a process for manufacturing carbamat-benzoxazinones of formula (I), and to the use of carbamat-benzoxazinones of formula (I) in manufacturing benzoxazinones of formula (X).

9 Claims, No Drawings

CARBAMAT-BENZOXAZINONES

This application is a National Stage application of International Application No. PCT/EP2013/066562, filed Aug. 7, 2013, which claims the benefit of U.S. Provisional Application No. 61/684,161 filed Aug. 17, 2012, the entire contents of which are hereby incorporated herein by reference. This application also claims priority under 35 U.S.C. §119 to European Patent Application No. 12180824.0 filed Aug. 17, 2012 the entire contents of which is hereby incorporated herein by reference.

The invention relates to carbamat-benzoxazinones of formula (I), a process for manufacturing the same and their use for manufacturing benzoxazinones.

There is an ongoing need for plant protection compounds, for example herbicides, since weeds cause tremendous global economic losses by reducing crop yields and lowering crop quality. Accordingly there is also a need for efficient and improved manufacturing processes allowing the preparation of such plant protection compounds, for example herbicides.

WO 11/057935 discloses carbamates as intermediates for the preparation of uracil-substituted benzoxazinones.

Surprisingly it has been found that carbamat-benzoxazinones of formula (I) are potential intermediates for the preparation of active ingredients, for example for the preparation of the herbicidal active ingredients as described in WO 10/145992.

Accordingly, the present invention relates to carbamat-benzoxazinones of formula (I),

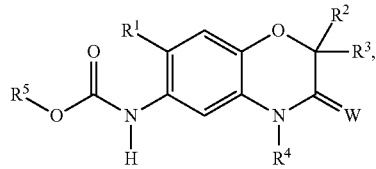

wherein
$R^1$ is H or halogen;
$R^2$ is halogen;
$R^3$ is H or halogen;
$R^4$ is H, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is aryl, 5- or 6-membered heteroaryl or aryl-$C_1$-$C_6$-alkyl,
wherein the aryl or heteroaryl rings are unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl; and
W is O or S.

Further the present invention relates to a process for the preparation of carbamat-benzoxazinones of formula (I) by reacting amino-benzoxazinones of formula (II) with compounds of formula (III), optionally in the presence of a base.

In a further aspect of the present invention there is provided the use of carbamat-benzoxazinones of formula (I) in manufacturing benzoxazinones of formula (X).

The organic moieties mentioned in the definition of the compounds and the substituents according to the invention, esp. of variables $R^1$ to $R^5$ are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:
$C_1$-$C_4$-alkyl: for example $CH_3$, $C_2H_5$, n-propyl, $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_3$-$C_6$-cycloalkyl-$C_1$-$C_6$-alkyl, $C_1$-$C_6$-cyanoalkyl, $C_1$-$C_6$-nitroalkyl, aryl-$C_1$-$C_6$-alkyl, $C_1$-$C_6$-alkylcarbonyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: a $C_3$-$C_6$-alkenyl radical as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxy-$C_1$-$C_6$-alkyl, $C_1$-$C_6$-alkoxycarbonyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as mentioned above, and also, for example, 5-fluoro-pentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

aryl and also the aryl moieties of aryl-$C_1$-$C_6$-alkyl: a mono- to trinuclear aromatic carbocycle having 6 to 14 ring members, such as for example phenyl, naphthyl, anthracenyl and phenanthrenyl;

5- or 6-membered heteroaryl: an aromatic 5- or 6-membered monocyclic heterocycle which, in addition to carbon atoms comprises one to three nitrogen atoms, one or two nitrogen atoms and one sulfur atom, one nitrogen and one oxygen atom, one oxygen atom, or one sulfur atom as ring members, for example 5-membered aromatic rings such as like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); and for example 6-membered aromatic rings such as pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl).

The preferred embodiments of the invention mentioned herein below have to be understood as being preferred either independently from each other or in combination with one another.

According to a preferred embodiment of the invention preference is given to those carbamat-benzoxazinones of formula (I), wherein the variables, either independently of one another or in combination with one another, have the following meanings:

$R^1$ is preferably H or F; particularly preferred H;
is also preferably halogen; especially preferred F or Cl; more preferred F;

$R^2$ is preferably Cl or F;
particularly preferred F;

$R^3$ is preferably H, Cl or F;
particularly preferred H or F; especially preferred H;
also preferred halogen, particularly preferred F or Cl, especially preferred F;

$R^4$ is preferably $C_3$-$C_6$-alkynyl or $C_3$-$C_6$-haloalkynyl, particularly preferred $C_3$-alkynyl or $C_3$-haloalkynyl, especially preferred $CH_2C\equiv CH$, $CH_2C\equiv CCl$ or $CH_2C\equiv CBr$;
is also preferably $C_3$-$C_6$-alkynyl or $C_3$-$C_6$-cycloalkyl-$C_1$-$C_6$-alkyl, particularly preferred propargyl or cyclopropylmethyl;
is also preferably H or $C_3$-$C_6$-alkynyl, particularly preferred H or $C_3$-alkynyl; especially preferred H or $CH_2C\equiv CH$; more preferred H; also more preferred $CH_2C\equiv CH$;
is also preferably $C_3$-$C_6$-haloalkynyl, particularly preferred $C_3$-haloalkynyl, especially preferred $CH_2C\equiv CCl$ or $CH_2C\equiv CBr$;

$R^5$ is preferably 5- or 6-membered heteroaryl or aryl-$C_1$-$C_6$-alkyl,
wherein the heteroaryl or aryl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;
particularly preferred 5- or 6-membered heteroaryl,
wherein the heteroaryl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;
also particularly preferred aryl-$C_1$-$C_6$-alkyl, wherein the aryl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;
especially preferred benzyl, wherein the benzyl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;

$R^5$ is also preferably phenyl or benzyl, wherein the phenyl or the benzyl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;
particularly preferred phenyl, wherein the phenyl ring is
unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl;
preferably unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred unsubstituted, partially or fully halogenated or substituted by one $C_1$-$C_6$-alkyl group;
especially preferred unsubstituted or substituted by one halogen atom or one $C_1$-$C_6$-alkyl group;
more preferred unsubstituted, substituted by one chlorine atom or by one $CH_3$ group;
most preferred unsubstituted;
also most preferred substituted by one chlorine atom;
also most preferred substituted by one $CH_3$ group;
especially preferred phenyl, wherein the phenyl ring is
partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
particularly preferred partially or fully halogenated or substituted by one $C_1$-$C_6$-alkyl group;
especially preferred substituted by one halogen atom or one $C_1$-$C_6$-alkyl group;
more preferred substituted by one chlorine atom or by one $CH_3$ group;

W is preferably O,
is also preferably S.

Particular preference is given to the carbamat-benzoxazinones of formula (I.a), which correspond to carbamat-benzoxazinones of formula (I) wherein $R^2$ is F, $R^5$ is phenyl and W is O:

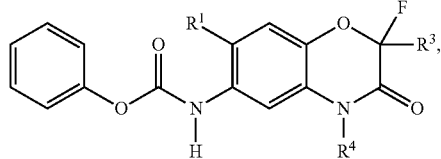

(I.a)

wherein the variables $R^1$, $R^3$ and $R^4$ have the meanings, in particular the preferred meanings, as defined above; special preference is given to the carbamat-benzoxazinones of formulae (I.a.1) to (I.a.54) of Table A listed below, in which the variables $R^1$, $R^3$ and $R^4$ together have the meanings given in one row of Table A (carbamat-benzoxazinones of formulae I.a.1 to I.a.54); and where the definitions of the variables $R^1$, $R^3$ and $R^4$ are of particular importance for the compounds, the process and the use of the compounds according to the invention not only in combination with one another but in each case also on their own:

TABLE A

| No. | $R^1$ | $R^3$ | $R^4$ |
|---|---|---|---|
| I.a.1 | H | H | H |
| I.a.2 | H | H | $CH_3$ |
| I.a.3 | H | H | $C_2H_5$ |
| I.a.4 | H | H | $CH_2$—$C_2H_5$ |
| I.a.5 | H | H | $CH(CH_3)_2$ |
| I.a.6 | H | H | $CH_2$—$CH_2$—$(CH_3)_2$ |
| I.a.7 | H | H | $CH_2$—$CH$=$CH_2$ |
| I.a.8 | H | H | $CH_2C$≡$CH$ |
| I.a.9 | H | H | $CH_2C$≡$C$—$Br$ |
| I.a.10 | H | F | H |
| I.a.11 | H | F | $CH_3$ |
| I.a.12 | H | F | $C_2H_5$ |
| I.a.13 | H | F | $CH_2$—$C_2H_5$ |
| I.a.14 | H | F | $CH(CH_3)_2$ |
| I.a.15 | H | F | $CH_2$—$CH_2$—$(CH_3)_2$ |
| I.a.16 | H | F | $CH_2$—$CH$=$CH_2$ |
| I.a.17 | H | F | $CH_2C$≡$CH$ |
| I.a.18 | H | F | $CH_2C$≡$C$—$Br$ |
| I.a.19 | F | H | H |
| I.a.20 | F | H | $CH_3$ |
| I.a.21 | F | H | $C_2H_5$ |
| I.a.22 | F | H | $CH_2$—$C_2H_5$ |
| I.a.23 | F | H | $CH(CH_3)_2$ |
| I.a.24 | F | H | $CH_2$—$CH_2$—$(CH_3)_2$ |
| I.a.25 | F | H | $CH_2$—$CH$=$CH_2$ |
| I.a.26 | F | H | $CH_2C$≡$CH$ |
| I.a.27 | F | H | $CH_2C$≡$C$—$Br$ |
| I.a.28 | F | F | H |
| I.a.29 | F | F | $CH_3$ |
| I.a.30 | F | F | $C_2H_5$ |
| I.a.31 | F | F | $CH_2$—$C_2H_5$ |
| I.a.32 | F | F | $CH(CH_3)_2$ |
| I.a.33 | F | F | $CH_2$—$CH_2$—$(CH_3)_2$ |
| I.a.34 | F | F | $CH_2$—$CH$=$CH_2$ |
| I.a.35 | F | F | $CH_2C$≡$CH$ |
| I.a.36 | F | F | $CH_2C$≡$C$—$Br$ |
| I.a.37 | Cl | H | H |
| I.a.38 | Cl | H | $CH_3$ |
| I.a.39 | Cl | H | $C_2H_5$ |
| I.a.40 | Cl | H | $CH_2$—$C_2H_5$ |
| I.a.41 | Cl | H | $CH(CH_3)_2$ |
| I.a.42 | Cl | H | $CH_2$—$CH_2$—$(CH_3)_2$ |
| I.a.43 | Cl | H | $CH_2$—$CH$=$CH_2$ |
| I.a.44 | Cl | H | $CH_2C$≡$CH$ |
| I.a.45 | Cl | H | $CH_2C$≡$C$—$Br$ |
| I.a.46 | Cl | F | H |
| I.a.47 | Cl | F | $CH_3$ |
| I.a.48 | Cl | F | $C_2H_5$ |
| I.a.49 | Cl | F | $CH_2$—$C_2H_5$ |
| I.a.50 | Cl | F | $CH(CH_3)_2$ |
| I.a.51 | Cl | F | $CH_2$—$CH_2$—$(CH_3)_2$ |
| I.a.52 | Cl | F | $CH_2$—$CH$=$CH_2$ |
| I.a.53 | Cl | F | $CH_2C$≡$CH$ |
| I.a.54 | Cl | F | $CH_2C$≡$C$—$Br$ |

Also particularly preferred are the carbamat-benzoxazinones of formula I.b, particularly preferred the carbamat-benzoxazinones of formulae I.b.1 to I.b.54, which differ from the corresponding carbamat-benzoxazinones of formulae I.a.1 to I.a.54 only in that $R^5$ is 4-chloro-phenyl:

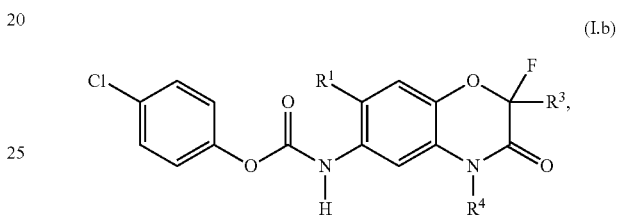

(I.b)

Also particularly preferred are the carbamat-benzoxazinones of formula I.c, particularly preferred the carbamat-benzoxazinones of formulae I.c.1 to I.c.54, which differ from the corresponding carbamat-benzoxazinones of formulae I.a.1 to I.a.54 only in that $R^5$ is 4-$CH_3$-phenyl:

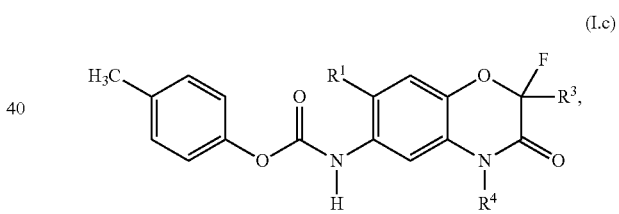

(I.c)

Also particularly preferred are the carbamat-benzoxazinones of formula I.d, particularly preferred the carbamat-benzoxazinones of formulae I.d.1 to I.d.54, which differ from the corresponding carbamat-benzoxazinones of formulae I.a.1 to I.a.54 only in that $R^5$ is 3-$CH_3$-phenyl:

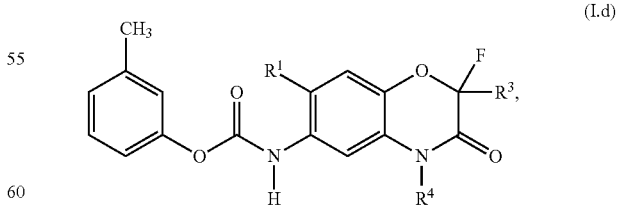

(I.d)

Also particularly preferred are the carbamat-benzoxazinones of formula I.e, particularly preferred the carbamat-benzoxazinones of formulae I.e.1 to I.e.54, which differ from the corresponding carbamat-benzoxazinones of formulae I.a.1 to I.a.54 only in that $R^5$ is 2-$CH_3$-phenyl:

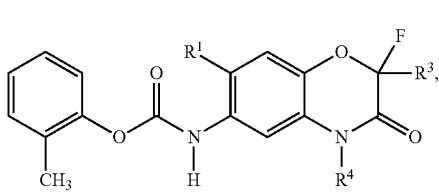
(I.e)

Also particularly preferred are the carbamat-benzoxazinones of formula (I.a.a), which correspond to carbamat-benzoxazinones of formula (I), wherein $R^1$, $R^2$ and $R^3$ are F, $R^5$ is phenyl and W is O:

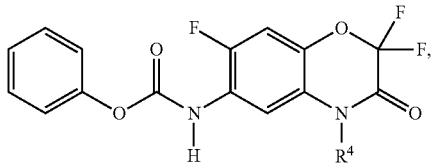
(I.a.a)

wherein $R^4$ is H or $C_3$-$C_6$-alkynyl, preferably is H or propargyl;

particularly preferred is H;

also preferably is $C_3$-$C_6$-alkynyl;

particularly preferred is propargyl.

More particular preference is given to the carbamat-benzoxazinones of formulae (I.a.28) and (I.a.35), as defined above:

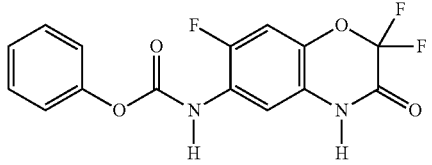
(I.a.28)

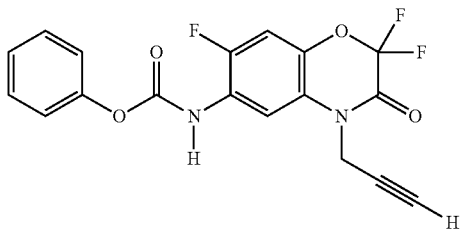
(I.a.35)

Very particular preference is given to the carbamat-benzoxazinone of formula (I.a.28).

Also very particular preference is given to the carbamat-benzoxazinone of formula (I.a.35).

Carbamat-benzoxazinones of formula (I) can be prepared by reacting amino-benzoxazinones of formula (II),

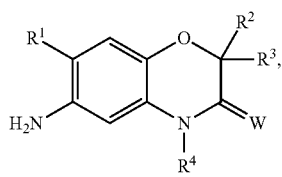
(II)

wherein $R^1$, $R^2$, $R^3$, $R^4$ and W are defined as in formula (I); with compounds of formula (III)

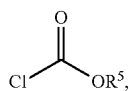
(III)

wherein $R^5$ is defined as in formula (I);
optionally in the presence of a base.

In case the reaction of the amino-benzoxazinones of formula (II) with compounds of formula (III), is conducted in the presence of a base, the reaction is generally carried out at a temperature in the range from −40° C. to the boiling point of the solvent used, for example from −40 to 150° C., preferably in the range from −20 to 100° C., more preferably in the range from 0 to 70° C.

In case the reaction of the amino-benzoxazinones of formula (II) with compounds of formula (III), is conducted in the absence of a base, the reaction is generally carried out at a temperature in the range from −40° C. to the boiling point of the solvent used, for example from −40 to 150° C., preferably in the range from 0 to 150° C., more preferably in the range from 50 to 130° C.

In case THF is used as the solvent, the reaction is preferably carried out at room temperature, i.e. at about 20° C.

In one embodiment of the process according to the invention, the compounds of formula (III) are used in excess with regard to the amino-benzoxazinones of formula (II).

In another embodiment of the process according to the invention, the compounds of formula (III) and the amino-benzoxazinones of formula (II) are used in equimolar amounts.

In another embodiment of the process according to the invention, the amino-benzoxazinones of formula (II) are used in excess with regard to the compounds of formula (III).

Preferably the molar ratio of the compounds of formula (III) to the amino-benzoxazinones of formula (II) is in the range from 0.9:1 to 1.5:1, preferably from 1.0:1 to 1.1:1.

In one embodiment the reaction of the amino-benzoxazinones of formula (II) with the compounds of formula (III) is carried out in the presence of a base.

Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal acetates such as lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium; alkyl magnesium halides such as methyl magnesium chloride and isopropyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium.

Examples of suitable nitrogen-containing bases are $C_1$-$C_6$-alkylamines, preferably trialkylamines, for example triethylamine, trimethylamine, N-ethyldiisopropylamine, ammonia, N-methylpiperidine, pyridine, substituted pyridines such as lutidine, collidine and 4-(dimethylamino)pyridine (DMAP), N-methylmorpholine, imidazole, 1,8-diazabicyclo[5.4.0]undec-7-ene (DBU) or 1,5-diazabicyclo[4.3.0]non-5-ene (DBN).

Preferred bases are tertiary amines and alkali metal and alkaline earth metal carbonates and bicarbonates as mentioned above.

Especially preferred bases are triethylamine and alkali metal and alkaline earth metal carbonates as mentioned above.

The term base as used herein also includes mixtures of two or more, preferably two of the above compounds. Particular preference is given to the use of one base.

The bases are generally employed in equimolar amounts; however they can also be employed in catalytic amounts, in excess or, if appropriate, be used as solvent.

In another embodiment the reaction of the amino-benzoxazinones of formula (II) with the compounds of formula (III) is carried out in the absence of a base. Such embodiment is preferred.

The reaction may in principle be carried out in substance. However, preference is given to reacting the amino-benzoxazinones (II) with the compounds of formula (III), and optionally a base in an organic solvent. Suitable in principle are all solvents which are capable of dissolving the amino-benzoxazinones (II) and the compounds of formula (III), and optionally a base at least partly and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, esters, aromatic hydrocarbons and nitriles as described above. Particularly preferred solvents are THF, ethyl acetate, toluene and acetonitrile.

Especially preferred solvents are ethyl acetate and toluene.

The term solvent as used herein also includes mixtures of two or more of the above solvents.

For the reaction, the amino-benzoxazinones of formula (II), the compounds of formula (III) and optionally the base may be contacted with one another in any desired manner, i.e. the reactants and optionally the base may be introduced into the reaction vessel separately, simultaneously or successively and reacted. For example, the amino-benzoxazinones of formula (II) and the compounds of formula (III) may be initially charged in a reaction vessel, if appropriate with the desired solvent, and then the desired reaction conditions may be attained. However, it is also possible to introduce the majority or entirety of the amino-benzoxazinones of formula (II) and subsequently add the compounds of formula (III), if appropriate in a solvent, under reaction conditions, into the reaction vessel.

In one embodiment of the process according to the invention, the compounds of formula (III) and optionally the base are initially charged in a reaction vessel, if appropriate with the desired solvent, and subsequently the amino-benzoxazinones of formula (II) are added, more preferably are added a little at a time, into the reaction vessel.

In another embodiment of the process according to the invention, the amino-benzoxazinones of formula (II) and optionally the base are initially charged in a reaction vessel, if appropriate with the desired solvent, and subsequently the compounds of formula (III) are added, more preferably are added a little at a time, into the reaction vessel. Such embodiment is preferred.

In a further preferred embodiment of the invention, the majority, in particular at least 80% and more preferably the entirety or virtually the entirety (>95%) of the amino-benzoxazinones of formula (II) and optionally the base are initially charged, and the majority, in particular at least 80% and more preferably the entirety or virtually the entirety (>95%) of the compounds of formula (III) is added thereto under reaction conditions in the course of the reaction, for example over a period of from 0.5 to 20 h and in particular from 1 to 10 h. To this end, the compounds of formula (III) will preferably be dissolved in a solvent.

The reaction can be carried out at atmospheric pressure, reduced pressure or under elevated pressure, if appropriate under an inert gas, continuously or batchwise.

It might be advantageous to partly, almost completely or completely remove the HCl formed in the course of the reaction.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

In case the reaction of the amino-benzoxazinones of formula (II) with compounds of formula (III), is conducted in the absence of a base, preferably the solvent and optionally the excess of compounds of formula (III) are removed by customary methods, e.g. by distillation.

Another option for work-up is to remove the HCl developed during the reaction in vacuo or by means of an inert gas flow, and then used the solution obtained without further purification in the subsequent reaction.

In case the reaction of the amino-benzoxazinones of formula (II) with compounds of formula (III) is conducted in the presence of a base, after the ending of the reaction, preferably in a further step the reaction mixture is diluted by addition of water followed by phase separation. The solvent can then be removed by customary methods.

Generally the product is obtained with high purity. If necessary, for further purification it is possible to employ the typical methods such as crystallization, precipitation (for example by addition of an apolar solvent such as pentane, cyclohexane, heptane or toluene, or mixtures of said solvents) or chromatography.

The amino-benzoxazinones of formula (II) necessary for the preparation of the carbamat-benzoxazinones of formula (I) can be prepared as follows:

The term "amino-benzoxazinones of formula (II)" combines NH-benzoxazinones of formula (II-1) (corresponding to amino-benzoxazinones of formula (II) wherein $R^4$ is H), and 4-substituted amino-benzoxazinones of formula (II-2) (corresponding to amino-benzoxazinones of formula (II) wherein $R^4$ is $R^\#$).

The 4-substituted amino-benzoxazinones of formula (II-2) necessary for the preparation of the carbamat-benzoxazinones of formula (I), wherein $R^4$ is $R^\#$, can be prepared by reacting NH-benzoxazinones of formula (II-1) with a base and compounds of formula (IV), $R^\# L^\#$:

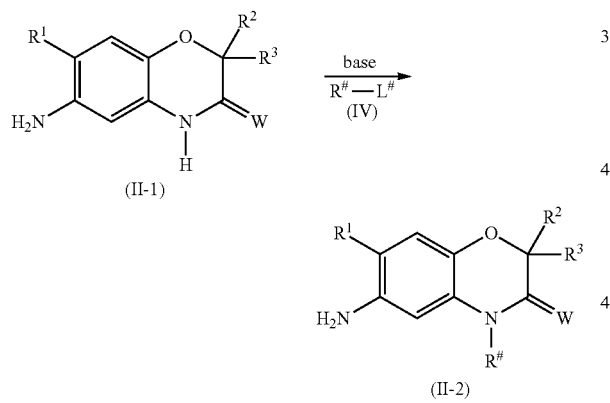

wherein
$R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$L^\#$ is halogen or $OS(O)_2R^9$;

$R^9$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy; and $R^1$, $R^2$, $R^3$ and W are defined as in formula (I) above.

The NH-benzoxazinones of formula (II-1) that are converted into the 4-substituted amino-benzoxazinones of formula (II-2) can also be used in the form of a salt, for example in form of their alkali metal and alkaline earth metal salt, preferably in the form of their lithium, sodium or potassium salts.

If a salt of the NH-benzoxazinone of formula (II-1) is used, the addition of a base is not necessary.

The compounds of formula (IV), $R^\# L^\#$, necessary for the preparation of the 4-substituted amino-benzoxazinones of formula (II-2), are commercially available or can be prepared by methods known in the art, see e.g. Houben-Weyl 1985, E11-2, page 1084.

Accordingly, in a further preferred embodiment of the process of the invention carbamat-benzoxazinones of formula (I), wherein $R^4$ is $R^\#$, are prepared by
a) reacting NH-benzoxazinones of formula (II-1) with a base and compounds of formula (IV), $R^\# L^\#$, to give 4-substituted amino-benzoxazinones of formula (II-2);
b) reacting the 4-substituted amino-benzoxazinones of formula (II-2) with compounds of formula (III) to give carbamat-benzoxazinones of formula (I), wherein $R^4$ is $R^\#$.

The NH-benzoxazinones of formula (II-1) (corresponding to amino-benzoxazinones of formula (II) wherein $R^4$ is H) necessary for the preparation of the carbamat-benzoxazinones of formula (I), wherein $R^4$ is H, or for the 4-substituted benzoxazinones of formula (II-2), can be prepared by reacting dinitro compounds of formula (VI-1) with a reducing agent to give diamino compounds of formula (V) and subsequently treating the diamino compounds of formula (V) with an acid:

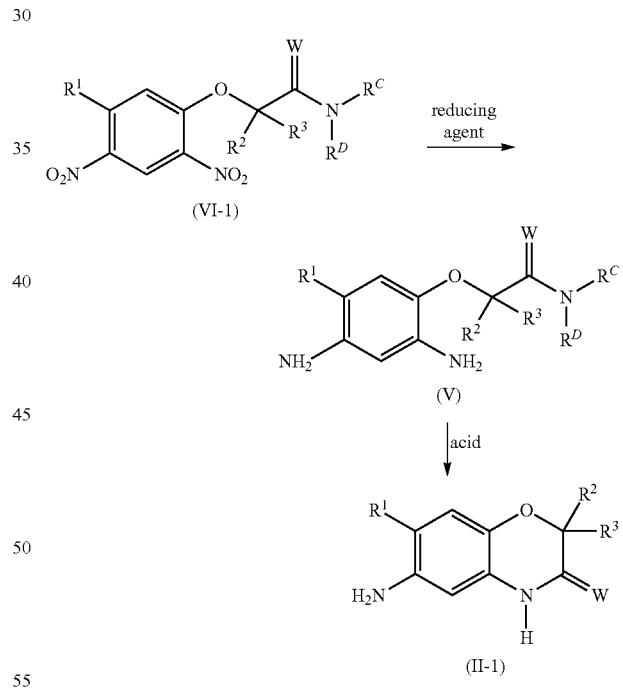

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)-amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents; and $R^1$, $R^2$, $R^3$ and W are defined as in formula (I) above.

Accordingly, in a further preferred embodiment of the process of the invention the carbamat-benzoxazinones of formula (I) wherein $R^4$ is H, are prepared by
a) reacting dinitro compounds of formula (VI-1) with a reducing agent to give diamino compounds of formula (V);
b) treating the diamino compounds of formula (V) with an acid to obtain NH-benzoxazinones of formula (II-1);
c) reacting the NH-benzoxazinones of formula (II-1) with compounds of formula (III) to give carbamat-benzoxazinones of formula (I), wherein $R^4$ is H.

Accordingly, in a further preferred embodiment of the process of the invention the carbamat-benzoxazinones of formula (I), wherein $R^4$ is $R^\#$ are prepared by
a) reacting dinitro compounds of formula (VI-1) with a reducing agent to give diamino compounds of formula (V);
b) treating the diamino compounds of formula (V) with an acid to obtain NH-benzoxazinones of formula (II-1);
c) reacting the NH-benzoxazinones of formula (II-1) with a base and compounds of formula (IV), $R^\#L^\#$, to give 4-substituted amino-benzoxazinone of formula (II-2);
d) reacting the 4-substituted amino-benzoxazinones of formula (II-2) with compounds of formula (III) to give carbamat-benzoxazinones of formula (I), wherein $R^4$ is $R^\#$.

Accordingly, in a further preferred embodiment of the process of the invention the carbamat-benzoxazinones of formula (I) are prepared by
a) reacting dinitro compounds of formula (VI-1) with a reducing agent to give diamino compounds of formula (V);
b) treating the diamino compounds of formula (V) with an acid to obtain NH-benzoxazinones of formula (II-1);
c) optionally reacting the NH-benzoxazinones of formula (II-1) with a base and compounds of formula (IV), $R^\#L^\#$, to give 4-substituted amino-benzoxazinone of formula (II-2);
d) reacting the amino-benzoxazinones of formula (II) with compounds of formula (III) to give carbamat-benzoxazinones of formula (I).

The dinitro compounds of formula (VI-1) necessary for preparing the diamino compounds of formula (V) can be obtained by reacting haloacetamides of formula (VII) with phenols of formula (VIII) in the presence of a base to give aryloxyacetamides of formula (VI) and, if $R^A$ and/or $R^B$ in formula (VI) are H, subsequently treating the aryloxyacetamides of formula (VI) with $HNO_3/H_2SO_4$:

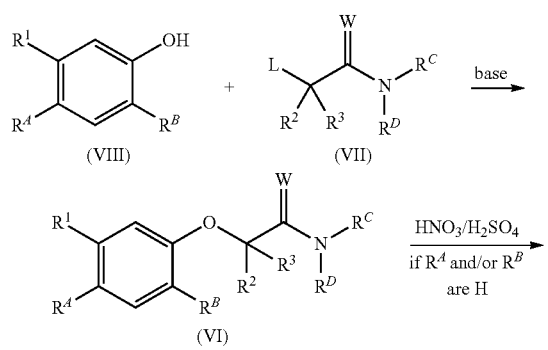

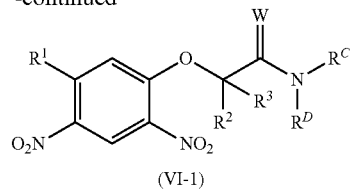

wherein
$R^A$, $R^B$ are independently H or $NO_2$;
L is halogen;
$R^1$, $R^2$, $R^3$ and W are defined as in formula (I) above; and
$R^C$ and $R^D$ are defined as above.

The haloacetamides of formula (VII) and the phenols of formula (VIII) are commercially available or can be prepared by methods known in the art.

The phenols of formula (VIII) that are converted into the aryloxyacetamides of formula (VI) can also be used in the form of a salt, for example in form of their alkali metal and alkaline earth metal salt, preferably in the form of their sodium, potassium, magnesium or calcium salt.

If a salt of the phenol of formula (VIII) is used, the addition of a base is not necessary.

Accordingly, in a further preferred embodiment of the process of the invention the carbamat-benzoxazinones of formula (I) wherein $R^4$ is H are prepared by
a) reacting haloacetamides of formula (VII) with phenols of formula (VIII) in the presence of a base to obtain aryloxyacetamides of formula (VI);
b) if $R^A$ and/or $R^B$ in formula (VI) are H, reacting the aryloxyacetamides of formula (VI) with $HNO_3/H_2SO_4$ to obtain dinitro compounds of formula (VI-1);
c) reacting the dinitro compounds of formula (VI-1) with a reducing agent to obtain diamino compounds of formula (V);
d) treating the diamino compounds of formula (V) with an acid to obtain NH-benzoxazinones of formula (II-1);
e) reacting the NH-benzoxazinones of formula (II-1) with compounds of formula (III) to give carbamat-benzoxazinones of formula (I), wherein $R^4$ is H.

Accordingly, in a further preferred embodiment of the process of the invention the carbamat-benzoxazinones of formula (I), wherein $R^4$ is $R^\#$ are prepared by
a) reacting haloacetamides of formula (VII) with phenols of formula (VIII) in the presence of a base to obtain aryloxyacetamides of formula (VI);
b) if $R^A$ and/or $R^B$ in formula (VI) are H, reacting the aryloxyacetamides of formula (VI) with $HNO_3/H_2SO_4$ to obtain dinitro compounds of formula (VI-1);
c) reacting the dinitro compounds of formula (VI-1) with a reducing agent to obtain diamino compounds of formula (V);
d) treating the diamino compounds of formula (V) with an acid to obtain NH-benzoxazinones of formula (II-1);
e) reacting the NH-benzoxazinones of formula (II-1) with a base and compounds of formula (IV) to obtain 4-substituted amino-benzoxazinones of formula (II-2);
f) reacting the 4-substituted amino-benzoxazinones of formula (II-2) with compounds of formula (III) to give carbamat-benzoxazinones of formula (I), wherein $R^4$ is $R^\#$.

Accordingly, in a further preferred embodiment of the process of the invention the carbamat-benzoxazinones of formula (I) are prepared by a) reacting haloacetamides of formula (VII) with phenols of formula (VIII) in the presence of a base to obtain aryloxyacetamides of formula (VI);
b) if $R^A$ and/or $R^B$ in formula (VI) are H, reacting the aryloxyacetamides of formula (VI) with $HNO_3/H_2SO_4$ to obtain dinitro compounds of formula (VI-1);
c) reacting the dinitro compounds of formula (VI-1) with a reducing agent to obtain diamino compounds of formula (V);
d) treating the diamino compounds of formula (V) with an acid to obtain NH-benzoxazinones of formula (II-1);
e) optionally reacting the NH-benzoxazinones of formula (II-1) with a base and compounds of formula (IV) to obtain 4-substituted amino-benzoxazinones of formula (II-2);
f) reacting the amino-benzoxazinones of formula (II) with compounds of formula (III) to give carbamat-benzoxazinones of formula (I).

With respect to the variables within the compounds of formulae (II-1), (II-2), (IV), (V), (VI), (VI-1), (VII) or (VIII), the particularly preferred embodiments of the compounds of formulae (II-1), (II-2), (IV), (V), (VI), (VI-1), (VII) or (VIII) correspond, either independently of one another or in combination with one another, to those of the substituents of formulae (I), (II) or (III), or have, either independently of one another or in combination with one another, the following meanings:

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
  wherein the phenyl and the benzyl ring are independently of one another unsubstituted or substituted by 1 to 3 substituents selected from the group consisting of halogen, $C_1$-$C_6$-alkyl or $C_1$-$C_6$-alkoxy,
  or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;
particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl,
  wherein the benzyl ring is unsubstituted or substituted by 1 to 3 substituents selected from the group consisting of halogen, $C_1$-$C_4$-alkyl or $C_1$-$C_4$-alkoxy,
  especially preferred the benzyl ring is unsubstituted,
  or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents;
L is preferably Cl, Br or I; particularly preferred Cl or Br; especially preferred Br;
$R^\#$ is preferably $C_3$-$C_6$-alkynyl or $C_3$-$C_6$-haloalkynyl; more preferably $C_3$-alkynyl or $C_3$-haloalkynyl; particularly preferred $CH_2C{\equiv}CH$, $CH_2C{\equiv}CCl$ or $CH_2C{\equiv}CBr$;
  is also preferably $C_3$-$C_6$-alkynyl or $C_3$-$C_6$-cycloalkyl-$C_1$-$C_6$-alkyl; particularly preferred propargyl or cyclopropylmethyl;
  is also preferably $C_3$-$C_6$-alkynyl; more preferably $C_3$-alkynyl; particularly preferred $CH_2C{\equiv}CH$;
  is also preferably $C_3$-$C_6$-haloalkynyl; more preferably $C_3$-haloalkynyl; particularly preferred $CH_2C{\equiv}CCl$ or $CH_2C{\equiv}CBr$;

$L^\#$ is preferably halogen or $OS(O_2)R^9$;
  wherein $R^9$ is $C_1$-$C_6$-alkyl, phenyl or phenyl-$C_1$-$C_6$-alkyl;
  wherein each phenyl ring independently of one another is unsubstituted or substituted by 1 to 3 $C_1$-$C_6$-alkyl substituents;
  is particularly preferred halogen or $OS(O_2)R^9$,
    wherein $R^9$ is $C_1$-$C_6$-alkyl or phenyl, wherein the phenyl ring is unsubstituted or substituted by 1 to 3 $C_1$-$C_6$-alkyl substituents;
  is especially preferred Cl, Br, $OS(O)_2CH_3$ or $OS(O)_2(C_6H_4)CH_3$.

The compounds of formula (III) necessary for the preparation of the carbamat-benzoxazinones of formula (I), are commercially available or can be prepared by methods known in the art, see e.g. J.-P-G. Senet, Science of Synthesis, 2005, 18, page 334.

The carbamat-benzoxazinones of formula (I) are useful in the synthesis of benzoxazinones of formula (X), which are herbicidal active ingredients as described in WO 10/145992.

Benzoxazinones of formula (X) can be prepared by reacting carbamat-benzoxazinones of formula (I) with carbamates of formula (IX) in the presence of a base:

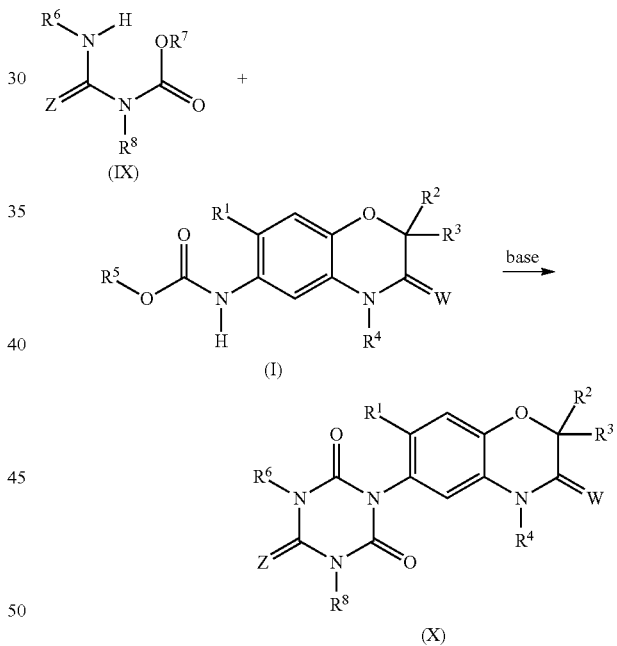

wherein
$R^1$, $R^2$, $R^3$, $R^4$, $R^5$ and W have the meanings, preferably the preferred meanings, as defined in formula (I) above; and
$R^6$ is H or $C_1$-$C_6$-alkyl;
$R^7$ is $C_1$-$C_6$-alkyl, $C_1$-$C_6$-haloalkyl, $C_1$-$C_6$-cyanoalkyl, $C_1$-$C_6$-nitroalkyl, aryl, 5- or 6-membered heteroaryl or aryl-$C_1$-$C_6$-alkyl,
  wherein the aryl or heteroaryl rings are unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl;

$R^8$ is H or $C_1$-$C_6$-alkyl;
and
Z is O or S.

Accordingly, in a further preferred embodiment of the invention the carbamat-benzoxazinones of formula (I) are used for the manufacture of benzoxazinones of formula (X) by reacting the carbamat-benzoxazinones of formula (I) with carbamates of formula (IX) to give benzoxazinones of formula (X).

With respect to the substituents within the benzoxazinones of formula (X),

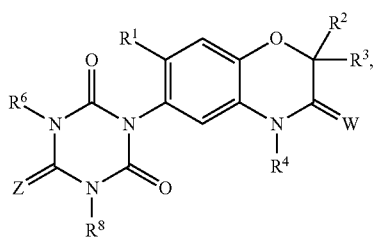

(X)

the particularly preferred embodiments of the benzoxazinones of formula (X) correspond, either independently of one another or in combination with one another, to those of the substituents of $R^1$, $R^2$, $R^3$, $R^4$ and W of formula (I); and
$R^6$ is preferably $C_1$-$C_6$-alkyl; more preferably $C_1$-$C_4$-alkyl; most preferably $CH_3$;
$R^8$ is preferably $C_1$-$C_6$-alkyl; more preferably $C_1$-$C_4$-alkyl; most preferably $CH_3$ and
Z is preferably O,
is also preferably S.

Particular preference is also given to the preparation of benzoxazinones of formula (X.a), which correspond to benzoxazinones of formula (X) wherein $R^2$ is F, $R^6$ and $R^8$ are $CH_3$, W is O and Z is S:

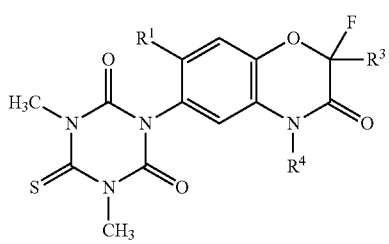

(X.a)

wherein the variables $R^1$, $R^3$ and $R^4$ have the meanings, in particular the preferred meanings, as defined above;
most preference to the preparation of benzoxazinones of formulae (X.a.1) to (X.a.54) of Table B listed below, in which the variables $R^1$, $R^3$ and $R^4$ together have the meanings given in one row of Table A (benzoxazinones of formulae X.a.1 to X.a.54); and where the definitions of the variables $R^1$, $R^3$ and $R^4$ are of particular importance for the compounds and the process according to the invention not only in combination with one another but in each case also on their own:

TABLE B

| No. | $R^1$ | $R^3$ | $R^4$ |
|---|---|---|---|
| X.a.1 | H | H | H |
| X.a.2 | H | H | $CH_3$ |
| X.a.3 | H | H | $C_2H_5$ |
| X.a.4 | H | H | $CH_2$—$C_2H_5$ |
| X.a.5 | H | H | $CH(CH_3)_2$ |
| X.a.6 | H | H | $CH_2$—$CH_2$—$(CH_3)_2$ |
| X.a.7 | H | H | $CH_2$—$CH$=$CH_2$ |
| X.a.8 | H | H | $CH_2C$≡$CH$ |
| X.a.9 | H | H | $CH_2C$≡$C$—Br |
| X.a.10 | H | F | H |
| X.a.11 | H | F | $CH_3$ |
| X.a.12 | H | F | $C_2H_5$ |
| X.a.13 | H | F | $CH_2$—$C_2H_5$ |
| X.a.14 | H | F | $CH(CH_3)_2$ |
| X.a.15 | H | F | $CH_2$—$CH_2$—$(CH_3)_2$ |
| X.a.16 | H | F | $CH_2$—$CH$=$CH_2$ |
| X.a.17 | H | F | $CH_2C$≡$CH$ |
| X.a.18 | H | F | $CH_2C$≡$C$—Br |
| X.a.19 | F | H | H |
| X.a.20 | F | H | $CH_3$ |
| X.a.21 | F | H | $C_2H_5$ |
| X.a.22 | F | H | $CH_2$—$C_2H_5$ |
| X.a.23 | F | H | $CH(CH_3)_2$ |
| X.a.24 | F | H | $CH_2$—$CH_2$—$(CH_3)_2$ |
| X.a.25 | F | H | $CH_2$—$CH$=$CH_2$ |
| X.a.26 | F | H | $CH_2C$≡$CH$ |
| X.a.27 | F | H | $CH_2C$≡$C$—Br |
| X.a.28 | F | F | H |
| X.a.29 | F | F | $CH_3$ |
| X.a.30 | F | F | $C_2H_5$ |
| X.a.31 | F | F | $CH_2$—$C_2H_5$ |
| X.a.32 | F | F | $CH(CH_3)_2$ |
| X.a.33 | F | F | $CH_2$—$CH_2$—$(CH_3)_2$ |
| X.a.34 | F | F | $CH_2$—$CH$=$CH_2$ |
| X.a.35 | F | F | $CH_2C$≡$CH$ |
| X.a.36 | F | F | $CH_2C$≡$C$—Br |
| X.a.37 | Cl | H | H |
| X.a.38 | Cl | H | $CH_3$ |
| X.a.39 | Cl | H | $C_2H_5$ |
| X.a.40 | Cl | H | $CH_2$—$C_2H_5$ |
| X.a.41 | Cl | H | $CH(CH_3)_2$ |
| X.a.42 | Cl | H | $CH_2$—$CH_2$—$(CH_3)_2$ |
| X.a.43 | Cl | H | $CH_2$—$CH$=$CH_2$ |
| X.a.44 | Cl | H | $CH_2C$≡$CH$ |
| X.a.45 | Cl | H | $CH_2C$≡$C$—Br |
| X.a.46 | Cl | F | H |
| X.a.47 | Cl | F | $CH_3$ |
| X.a.48 | Cl | F | $C_2H_5$ |
| X.a.49 | Cl | F | $CH_2$—$C_2H_5$ |
| X.a.50 | Cl | F | $CH(CH_3)_2$ |
| X.a.51 | Cl | F | $CH_2$—$CH_2$—$(CH_3)_2$ |
| X.a.52 | Cl | F | $CH_2$—$CH$=$CH_2$ |
| X.a.53 | Cl | F | $CH_2C$≡$CH$ |
| X.a.54 | Cl | F | $CH_2C$≡$C$—Br |

More particular preference is given to the preparation of the benzoxazinones of formulae (X.a.28) and (X.a.35) as defined above:

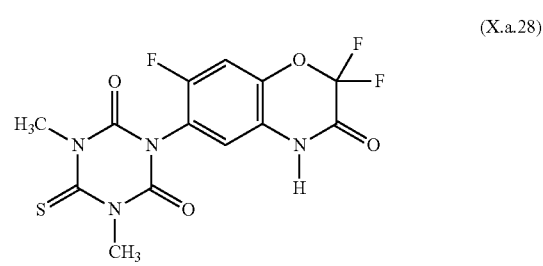

(X.a.28)

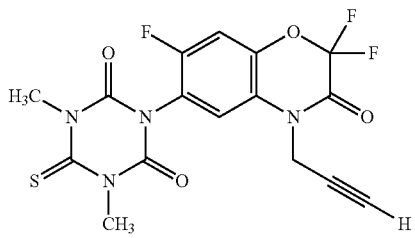
(X.a.35)

Very particular preference is given to the preparation of the benzoxazinone of formula (X.a.28) as defined above.

Also very particular preference is given to the preparation of the benzoxazinone of formula (X.a.35) as defined above.

The reaction of the carbamat-benzoxazinones of formula (I) with the carbamates of formula (IX) in the presence of a base is generally carried out at a temperature in the range of from −20° C. to the boiling point of the solvent used; preferably in the range from −20 to 150° C., particularly preferred in the range of from 0 to 120° C., more preferably in the range of from 20 to 80° C.

In one embodiment of the process according to the invention, the carbamates of formula (IX) and the carbamat-benzoxazinones of formula (I) are used in equimolar amounts.

In another embodiment of the process according to the invention, the carbamat-benzoxazinones of formula (I) are used in excess with regard to the carbamates of formula (IX).

In another embodiment of the process according to the invention, the carbamates of formula (IX) are used in excess with regard to the carbamat-benzoxazinones of formula (I). This embodiment is preferred.

Preferably the molar ratio of the carbamates of formula (IX) to the carbamat-benzoxazinones of formula (I) is in the range from 1.5:1 to 1:0.9, preferably 1.1:1 to 1:0.9, especially preferred 1:0.9, also especially preferred 1:1.

The reaction of the carbamates of formula (IX) with the carbamat-benzoxazinones of formula (I) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal aryloxides such as sodium phenolate and potassium phenolate; and furthermore organic bases, such as ammonia, tertiary amines like $C_1$-$C_6$-alkylamines, preferably trialkylamines, such as trimethylamine, triethylamine, diisopropylethylamine, N-ethyldiisopropylamine; and also N-methylpiperidine, 4-(dimethylamino)pyridine (DMAP), imidazole, pyridine, substituted pyridines such as collidine, lutidine, N-methylmorpholine and 4-dimethylaminopyridine and also bicyclic amines, such as 1,8-diazabicyclo[5.4.0]undec-7-ene (DBU) or 1,5-diazabicyclo[4.3.0]non-5-ene (DBN)

Preferred bases are alkali metal and alkaline earth metal aryloxides, alkali metal and alkaline earth metal carbonates and alkali metal and alkaline earth metal acetates as defined above.

Especially preferred bases are alkali metal and alkaline earth metal aryloxides, and alkali metal and alkaline earth metal acetates as defined above.

The term base as used herein also includes mixtures of two or more, preferably two of the above compounds. Particular preference is given to the use of one base.

The bases are generally employed in catalytic amounts based on the carbamat-benzoxazinones of formula (I), however they can also be employed in equimolar amounts or in excess.

Preferably the amount of base is from 1.5 mole equivalents to catalytic amounts, more preferably from 0.3 to 0.01 mole equivalents, especially preferred from 0.3 to 0.1 mole equivalents based on the carbamat-benzoxazinones of formula (I).

The reaction of the carbamates of formula (IX) with the carbamat-benzoxazinones of formula (I) and a base is usually carried out in a solvent. However the reaction in melt is possible in principle as well.

Suitable in principle are all solvents which are capable of dissolving the carbamates of formula (IX) and the carbamat-benzoxazinones of formula (I) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; dipolar aprotic solvents such as sulfolane, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are esters and dipolar aprotic solvents as described above.

More preferred solvents are ethyl acetate and DMF.

The term solvent as used herein also includes mixtures of two or more of the above compounds.

For the reaction, the carbamates of formula (IX), the carbamates-benzoxazinones of formula (I) and the base may be contacted with one another in any desired manner, i.e. the reactants and the base may be introduced into the reaction vessel separately, simultaneously or successively and reacted.

For example, the carbamates of formula (IX) and the carbamates-benzoxazinones of formula (I) may be initially charged in a reaction vessel, if appropriate with the desired solvent, and then the desired reaction conditions may be attained. However, it is also possible to introduce the majority or entirety of the carbamates of formula (IX) and subsequently add the carbamates-benzoxazinones of formula (I), if appropriate in a solvent, under reaction conditions, into the reaction vessel.

It might be advantageous, to add the base a little at a time.

In one embodiment of the process according to the invention, the carbamat-benzoxazinones of formula (I) and the base are initially charged in a reaction vessel, if appropriate with the desired solvent, and subsequently the carbamates of formula (IX) are added into the reaction vessel.

In a preferred embodiment of the process according to the invention, the carbamates of formula (IX) and the base are initially charged in a reaction vessel, if appropriate with the desired solvent, and subsequently the carbamat-benzoxazinones of formula (I) are added into the reaction vessel.

In a further particular embodiment of the process according to the invention, in case $R^7$ within the carbamates of formula (IX) is $C_1$-$C_6$-alkyl, especially preferred methyl, the carbamates of formula (IX) and the base are initially charged in a reaction vessel, if appropriate with the desired solvent, and subsequently the carbamat-benzoxazinones of formula (I) are added, more preferably are added a little at a time, into the reaction vessel.

In a further preferred embodiment of the invention, the majority, in particular at least 80% and more preferably the entirety or virtually the entirety (>95%) of the carbamates of formula (IX) and the base are initially charged, and the majority, in particular at least 80% and more preferably the entirety or virtually the entirety (>95%) of the carbamat-benzoxazinones of formula (I) is added thereto under reaction conditions in the course of the reaction, for example over a period from 0.5 to 20 h and in particular from 1 to 10 h. To this end, the carbamat-benzoxazinones of formula (I) will preferably be dissolved in a solvent.

In another preferred embodiment of the process according to the invention, the carbamates of formula (IX) and the carbamat-benzoxazinones of formula (I) are initially charged in a reaction vessel, if appropriate with the desired solvent, and subsequently the base is added into the reaction vessel.

The reaction temperature within such preferred embodiment is preferably in the range from 0 to 120° C., more preferably in the range from 20 to 80° C.

Such embodiment is particularly preferred in case $R^7$ within the carbamate of formula (IX) is aryl, especially preferred phenyl.

In a further preferred embodiment of the invention, the carbamates of formula (IX) and the carbamates-benzoxazinones of formula (I) are initially charged and then the majority, in particular at least 80% and more preferably the entirety or virtually the entirety (>95%), of the base is added thereto. The reaction may if appropriate be completed by metering in further base.

The reaction can be carried out at atmospheric pressure, reduced pressure or under elevated pressure, if appropriate under an inert gas, continuously or batch-wise.

Preference is given to partly or completely removing the compound $R^7O$—H formed in the course of the reaction of the carbamates of formula (IX) with carbamat-benzoxazinones of formula (I), especially when the compound $R^7O$—H is a $C_1$-$C_4$-alkanol such as methanol or ethanol.

To this end, the reaction will be carried out in a manner known per se at a temperature and a pressure at which the compounds $R^7O$—H, if appropriate, are partly or completely distilled out of the reaction mixture, optionally as an azeotrope with the solvent.

If appropriate, fresh solvent can be introduced into the mixture for compensation or the solvent distilled off with the compounds $R^7O$—H can be recycled into the reaction after optional distillative depletion of the compounds $R^7O$—H.

For these reasons, it is advantageous when the solvent used has a boiling point of at least 10° C., in particular at least 30° C., above the boiling point of the compounds $R^7O$—H formed in the reaction (each at atmospheric pressure).

Appropriately, the reaction of the carbamates of formula (IX) with carbamat-benzoxazinones of formula (I) is carried out in an apparatus which is equipped with at least one distillation or rectification apparatus, for example a distillation column, which firstly allows the compound $R^7O$—H, if appropriate together with the solvent, to be distilled off and simultaneously enables removal and recycling of any solvent distilled off with the compound $R^7O$—H.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

For further purification it is possible to employ the typical methods such as crystallization, precipitation (for example by addition of an apolar solvent such as pentane, cyclohexane, heptane or toluene, or mixtures of said solvents) or chromatography.

In a preferred embodiment of the reaction, in case the reaction has been carried out in DMF, the reaction mixture will generally be concentrated and/or cooled and/or a precipitant will be added.

Suitable precipitants are solvents in which the benzoxazinones of formula (X) dissolve only to a slight extent, if at all, at least at temperatures below 25° C.

These include in particular alcohols such as methanol, ethanol, n-propanol, isopropanol, n-butanol, isobutanol, tert.-butanol, water, and the like; or mixtures thereof;

preferably methanol, isobutanol and water, or mixtures thereof.

The precipitation or crystallization may be followed by further purification measures.

In another variant of the reaction in the process according to the invention and depending on the base used, after the ending of the reaction, it might be advantageous to dilute the reaction mixture by addition of water and/or acids, the pH of the aqueous phase being adjusted to pH in between 6 to 8, preferably pH=7.

Acids suitable for this purpose are organic acids and aqueous mineral acids known to the skilled worker, such as acetic acid, hydrochloric acid, sulfuric acid, nitric acid or phosphoric acid, for example.

The reaction mixture can then be worked up by the methods customary therefor. In general, the phases are separated and the solvent used will be removed by customary processes, for example by distillation. For further purification, the customary processes such as for example crystallization (for example also by addition of a nonpolar solvent such as pentane, cyclohexane, heptane or toluene, or mixtures of the solvents mentioned) can be employed.

With respect to the substituents within the carbamates of formula (IX), $$\begin{array}{c} R^6\diagdown_N\diagup^H \quad OR^7 \\ | \quad\quad | \\ Z\diagdown\quad\diagup N\diagdown \\ \quad\quad | \quad\quad O \\ \quad\quad R^8 \end{array} \quad (IX)$$

necessary for the use of the carbamat-benzoxazinones of formula (I) to prepare benzoxazinones of formula (X) according to the invention, the particularly preferred embodiments of the carbamates of formula (IX) correspond, either independently of one another or in combination with one another, to those of the variables of $R^6$, $R^8$ and Z of the benzoxazinones of formula (X); and $R^7$ is preferably $C_1$-$C_6$-alkyl, aryl, 5- or 6-membered heteroaryl or aryl-$C_1$-$C_6$-alkyl, wherein the heteroaryl or aryl ring is
  unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
  particularly preferred unsubstituted, partially or fully halogenated or substituted by one $C_1$-$C_6$-alkyl group;
  especially preferred unsubstituted or substituted by one halogen atom or one $C_1$-$C_6$-alkyl group;
  more preferred unsubstituted, substituted by one chlorine atom or by one $CH_3$ group;
  most preferred unsubstituted;
  also most preferred substituted by one chlorine atom;
  also most preferred substituted by one $CH_3$ group;
  particularly preferred $C_1$-$C_6$-alkyl or aryl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also particularly preferred aryl or aryl-$C_1$-$C_6$-alkyl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also particularly preferred $C_1$-$C_6$-alkyl or aryl-$C_1$-$C_6$-alkyl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  especially preferred $C_1$-$C_6$-alkyl;
  more preferred $CH_3$;
  also especially preferred aryl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also especially preferred aryl-$C_1$-$C_6$-alkyl, wherein the aryl-$C_1$-$C_6$-alkyl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;

$R^7$ is also preferably $C_1$-$C_6$-alkyl, phenyl or benzyl,
  more preferably methyl, ethyl, phenyl or benzyl,
  especially preferably methyl, phenyl or benzyl,
  wherein the phenyl or the benzyl ring is
    unsubstituted, partially or fully halogenated or substituted by one $C_1$-$C_6$-alkyl group, particularly preferred unsubstituted or substituted by one halogen atom or one $C_1$-$C_6$-alkyl group;
    especially preferred unsubstituted, substituted by one chlorine atom or by one $CH_3$ group;
    more preferred unsubstituted;
    also more preferred substituted by one chlorine atom,
    also more preferred substituted by one $CH_3$ group;
  particularly preferred $C_1$-$C_6$-alkyl or phenyl, wherein the phenyl ring is
    unsubstituted, partially or fully halogenated or substituted by one $C_1$-$C_6$-alkyl group, particularly preferred unsubstituted or substituted by one halogen atom or one $C_1$-$C_6$-alkyl group;
    especially preferred unsubstituted, substituted by one chlorine atom or by one $CH_3$ group;
    more preferred unsubstituted;
    also more preferred substituted by one chlorine atom,
    also more preferred substituted by one $CH_3$ group;

also particularly preferred phenyl or benzyl, wherein the phenyl or the benzyl ring is
  unsubstituted, partially or fully halogenated or substituted by one $C_1$-$C_6$-alkyl group, particularly preferred unsubstituted or substituted by one halogen atom or one $C_1$-$C_6$-alkyl group;
  especially preferred unsubstituted, substituted by one chlorine atom or by one $CH_3$ group;
  more preferred unsubstituted;
  also more preferred substituted by one chlorine atom,
  also more preferred substituted by one $CH_3$ group;
also particularly preferred $C_1$-$C_6$-alkyl or benzyl, wherein the benzyl ring is
  unsubstituted, partially or fully halogenated or substituted by one $C_1$-$C_6$-alkyl group, particularly preferred unsubstituted or substituted by one halogen atom or one $C_1$-$C_6$-alkyl group;
  especially preferred unsubstituted, substituted by one chlorine atom or by one $CH_3$ group;
  more preferred unsubstituted;
  also more preferred substituted by one chlorine atom,
  also more preferred substituted by one $CH_3$ group;
especially preferred phenyl, wherein the phenyl ring is
  unsubstituted, partially or fully halogenated or substituted by one $C_1$-$C_6$-alkyl group, particularly preferred unsubstituted or substituted by one halogen atom or one $C_1$-$C_6$-alkyl group;
  especially preferred unsubstituted, substituted by one chlorine atom or by one $CH_3$ group;
  more preferred unsubstituted;
  also more preferred substituted by one chlorine atom,
  also more preferred substituted by one $CH_3$ group.

Particular preference is also given to carbamates of formulae (IX.1) to (IX.8) of Table C listed below, in which the variables $R^6$, $R^7$, $R^8$ and Z together have the meanings given in one row of Table C (carbamates of formulae IX.1 to IX.8); and where the definitions of the variables $R^6$, $R^7$, $R^8$ and Z are of particular importance for the compounds according to the invention not only in combination with one another but in each case also on their own:

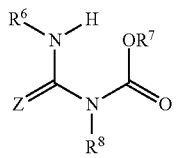
(IX)

TABLE C

| No. | $R^6$ | $R^7$ | $R^8$ | Z |
|---|---|---|---|---|
| IX.1 | $CH_3$ | $CH_3$ | $CH_3$ | O |
| IX.2 | $CH_3$ | $C_2H_5$ | $CH_3$ | O |
| IX.3 | $CH_3$ | $C_6H_5$ | $CH_3$ | O |
| IX.4 | $CH_3$ | $CH_2$—$C_6H_5$ | $CH_3$ | O |
| IX.5 | $CH_3$ | $CH_3$ | $CH_3$ | S |
| IX.6 | $CH_3$ | $C_2H_5$ | $CH_3$ | S |
| IX.7 | $CH_3$ | $C_6H_5$ | $CH_3$ | S |
| IX.8 | $CH_3$ | $CH_2$—$C_6H_5$ | $CH_3$ | S |

More particular preference is given to the carbamates of formulae (IX.5) and (IX.7) as defined above:

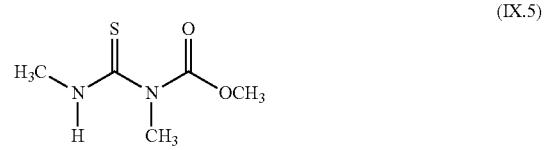
(IX.5)

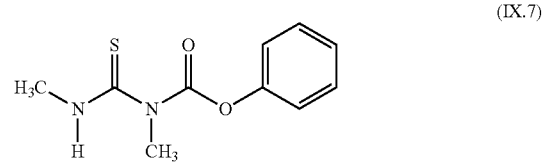
(IX.7)

Very particular preference is given to the carbamate of formula (IX.5) as defined above.

Also very particular preference is given to the carbamate of formula (IX.7) as defined above.

The carbamates of formula (IX) necessary for the use of the carbamat-benzoxazinones of formula (I) to prepare benzoxazinones of formula (X) can be prepared by reacting (thio)urea compounds of formula (XI) with chloroformic acid esters of formula (XII):

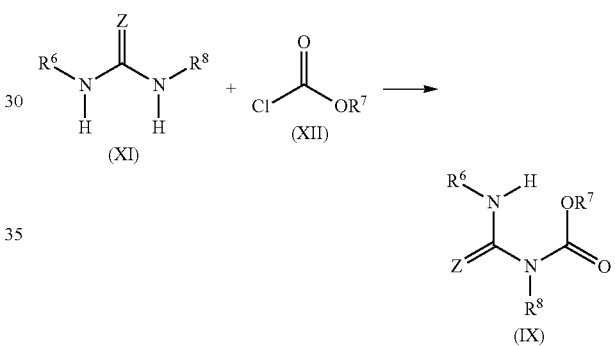

The reaction of the (thio)urea compounds of formula (XI) with the chloroformic acid ester of formula (XII), in the presence a base is generally carried out at a temperature in the range from –10 to 130° C., preferably in the range from 15 to 110° C., more preferably in the range from 20 to 80° C.

In one embodiment of the process according to the invention, the chloroformic acid esters of formula (XII) are used in excess with regard to the (thio)urea compounds of formula (XI).

In another embodiment of the process according to the invention, the chloroformic acid esters of formula (XII) and the (thio)urea compound of formula (XI) are used in equimolar amounts.

In another embodiment of the process according to the invention, the (thio)urea compounds of formula (XI) are used in excess with regard to the chloroformic acid esters of formula (XII).

Preferably the molar ratio of the chloroformic acid esters of formula (XII) to the (thio)urea compound of formula (XI) is in the range from 0.9:1 to 1.5:1, preferably from 1.05:1 to 1.15:1, especially preferred 1.1:1, more preferred 1.05:1.

The reaction of the (thio)urea compounds of formula (XI) with the chloroformic acid ester of formula (XII) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide; alkali metal and alkaline earth metal acetates such as lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride and isopropyl magnesium chloride, as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates, alkali metal hydrogen carbonates (bicarbonates) and $C_1$-$C_6$-alkylamines.

Especially preferred bases are alkali metal and alkaline earth metal carbonates and alkali metal hydrogen carbonates (bicarbonates).

The term base as used herein also includes mixtures of two or more, preferably two of the above compounds. Particular preference is given to the use of one base.

The bases are generally employed in equimolar amounts, however they can also be employed in excess or, if appropriate, be used as solvent.

Preferably the bases are used in excess, more preferably the ratio of the (thio)urea compound (XI) to the base is in the range from 1:2, preferably from 1:1.8, particularly preferred 1:1.1 mole equivalents based on the (thio)urea compound of the formula (XI).

It may be advantageous to add the base offset over a period of time.

The reaction of the (thio)urea compounds of formula (XI) with the chloroformic acid esters of formula (XII) and a base is carried out in a solvent.

Suitable in principle are all solvents which are capable of dissolving the (thio)urea compounds of formula (XI) and the chloroformic acid esters of formula (XII) at least partly and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, aromatic hydrocarbons, nitriles and esters as defined above. Particularly preferred solvents are THF, toluene, acetonitrile and ethylacetate.

The term solvent as used herein also includes mixtures of two or more of the above solvents.

For the reaction, the (thio)urea compounds of formula (XI), the chloroformic acid esters of formula (XII) and the base may be contacted with one another in any desired manner, i.e. the reactants and the base may be introduced into the reaction vessel separately, simultaneously or successively and reacted. For example, the (thio)urea compounds of formula (XI) and the chloroformic acid esters of formula (XII) may be initially charged in a reaction vessel, if appropriate with the desired solvent, and then the desired reaction conditions may be attained. However, it is also possible to introduce the majority or entirety of the (thio)urea compounds of formula (XI) and subsequently add the chloroformic acid esters of formula (XII), if appropriate in a solvent, under reaction conditions, into the reaction vessel.

It might be advantageous, to add the base a little at a time.

In one embodiment of the process according to the invention, the chloroformic acid esters of formula (XII) and the base are initially charged in a reaction vessel, if appropriate with the desired solvent, and subsequently the (thio)urea compounds of formula (XI) are added, more preferably are added a little at a time, into the reaction vessel.

In a preferred embodiment of the process according to the invention, the (thio)urea compounds of formula (XI) and the base are initially charged in a reaction vessel, if appropriate with the desired solvent, and subsequently the chloroformic acid esters of formula (XII) are added, more preferably are added a little at a time, into the reaction vessel.

Such embodiment is particularly preferred in case $R^7$ within the chloroformic acid esters of formula (XII) is $C_1$-$C_6$-alkyl, especially preferred methyl.

In a further preferred embodiment of the invention, the majority, in particular at least 80% and more preferably the entirety or virtually the entirety (>95%) of the (thio)urea compounds of formula (XI) and the base are initially charged, and the majority, in particular at least 80% and more preferably the entirety or virtually the entirety (>95%) of the chloroformic acid esters of formula (XII) is added thereto under reaction conditions in the course of the reaction, for example over a period from 0.5 to 20 h and in particular from 1 to 10 h. To this end, the chloroformic acid esters of formula (XII) will preferably be dissolved in a solvent.

In another preferred embodiment of the process according to the invention, the (thio)urea compounds of formula (XI) and the chloroformic acid esters of formula (XII) are initially charged in a reaction vessel, if appropriate with the desired solvent, and subsequently the base is added into the reaction vessel; more preferably is added into the reaction vessel a little at a time.

Such embodiment is particularly preferred in case $R^7$ within the chloroformic acid esters of formula (XII) is aryl, especially preferred phenyl.

In a further preferred embodiment of the invention, the (thio)urea compounds of formula (XI) and the chloroformic acid esters of formula (XII) are initially charged and then the majority, in particular at least 80% and more preferably the entirety or virtually the entirety (>95%), of the base is added thereto. The reaction may if appropriate be completed by metering in further base.

The reaction can be carried out at atmospheric pressure, reduced pressure or under elevated pressure, if appropriate under an inert gas, continuously or batch-wise.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

For further purification it is possible to employ the typical methods such as crystallization, precipitation (for example by addition of an apolar solvent such as pentane, cyclohexane, heptane or toluene, or mixtures of said solvents) or chromatography.

The (thio)urea compounds of formula (XI) necessary for the preparation of the carbamates of formula (IX) are commercially available or can be prepared by methods known in the art.

The chloroformic acid esters of formula (III) necessary for the preparation of the carbamates of formula (II) are commercially available.

The invention is illustrated by the following examples without being limited thereto or thereby.

EXAMPLES

The yields of the carbamat-benzoxazinones of formula (I), the carbamates of formula (IX) and the benzoxazinones of formula (X) were, unless stated otherwise, determined by means of quantitative HPLC:

Method A
Sample Preparation:
  The samples of the products to be determined were weighed into a 100 ml standard flask which was made up to 100 ml with acetonitril.
Chromatographic Conditions:
  Column: Zorbax Eclipse XDB-C18 1.8 µm 50×4.6 mm from Agilent®
  Wavelength: 210 nm
  Eluent: gradient of A (0.1% by volume of $H_3PO_4$ in $H_2O$) and B (0.1% by volume of $H_3PO_4$ in acetonitrile); starting with 2% B, then B rising from 2% to 30% within 2 min, then B rising from 30% to 100% within 6 min, then 2 min 100% B, then back to 2% within 0.1 min.
  Flow rate: 1.4 ml/min
  Pressure: approx. 210 bar Calibration:
  The calibration was effected with external standard. To establish the standard, a total of 5 samples of the pure substances were weighed in the following concentrations (precision+/−0.1 mg): approx. 0.02 g/l, approx. 0.04 g/l, approx. 0.06 g/l, approx. 0.08 g/l, approx. 0.10 g/l. With the aid of a suitable PC program, a calibration line was established. For the substances detailed above, this was a linear function. Standard deviation, correlation coefficient and straight-line equation were calculated. For each of the components, their concentration can thus be determined based on the particular external standard.

Method B)
Sample Preparation:
  The samples of the products to be determined were weighed into a 100 ml standard flask which was made up to 100 ml with acetonitril.
Chromatographic Conditions:
  Column: Zorbax SB-Phenyl 1.8 µm 50×4.6 mm from Agilent®
  Wavelength: 210 nm
  Eluent: gradient of A (0.1% by volume of $H_3PO_4$ in $H_2O$) and B (acetonitrile); starting with 15% B, then B rising from 15% to 50% within 5 min, then B rising from 50% to 100% within 5 min, then 2 min 100% B, then back to 15% within 0.1 min.
  Flow rate: 1.3 ml/min
  Pressure: approx. 365 bar
Calibration:
  The calibration was effected with external standard. To establish the standard, a total of 5 samples of the pure substances were weighed in the following concentrations (precision+/−0.1 mg): approx. 0.01 g/l, approx. 0.05 g/l, approx. 0.10 g/l, approx. 0.15 g/l, approx. 0.20 g/l. With the aid of a suitable PC program, a calibration line was established. For the substances detailed above, this was a linear function. Standard deviation, correlation coefficient and straight-line equation were calculated. For each of the components, their concentration can thus be determined based on the particular external standard.

1. Preparation of Carbamat-Benzoxazinones of Formula (I)

Examples 1.1 to 1.5

Phenyl N-(2,2,7-trifluoro-3-oxo-4-prop-2-ynyl-1,4-benzoxazin-6-yl)carbamate

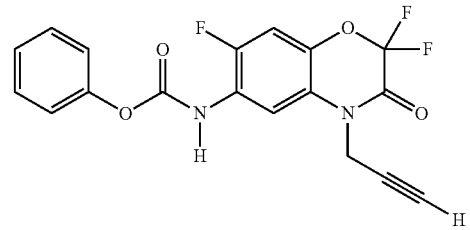 [SMILES: C#CCN1C(=O)C(F)(F)Oc2cc(F)c(NC(=O)Oc3ccccc3)cc21]

Example 1.1

182.9 g (0.700 mol) 6-Amino-2,2,7-trifluoro-4-prop-2-ynyl-4H-benzo[1,4]oxazin-3-one with a purity of 98.1% were dissolved in 521.1 g toluene and heated to reflux (110° C.) under agitation. 122.1 g (0.780 mol) phenyl chloroformate were added over 1 h at 107-112° C. (reflux) and the mixture afterwards poststirred over 1 h at the same temperature (HCl offgas). Low boilers were removed with a rotary evaporator under vacuum. 281.3 g (0.707 mol) of the product were obtained with 94.6% purity determined by quantitative HPLC method A ($t_R$=5.7 min; corresponding chemical yield 100%).

1H-NMR (500 MHz, CDCl$_3$): δ (ppm)=2.31 (t, 1H), 4.76 (d, 2H), 7.07 (d, 1H), 7.19-7.31 (m, 4H), 7.43 (t, 2H), 8.28 (d, 1H).

Example 1.2

53.2 g (0.200 mol) 6-Amino-2,2,7-trifluoro-4-prop-2-ynyl-4H-benzo[1,4]oxazin-3-one with a purity of 96.3% were dissolved in 500 mL acetonitrile. 18.48 g (0.22 mol) sodium bicarbonate were added. 34.4 g (0.22 mol) phenyl chloroformate were added slowly at 22° C. and the temperature was kept constant by an ice bath. The mixture was stirred for 3 h at room temperature. The solids were removed by filtration. 500 mL dichloromethane were added to the solution and the organic phase was washed three times with water. The organic phase was dried over MgSO$_4$ and evaporated to dryness. The residue was triturated with warm cyclohexane. The residue was removed by filtration and washed with cyclohexane. 74.0 g of the product were obtained as off-white solid, with a purity of 96.3% determined by quantitative HPLC method A ($t_R$=5.7 min), which corresponds to a chemical yield of 94.7%.

Example 1.3

1.5 g (5.8 mmol) 6-Amino-2,2,7-trifluoro-4-prop-2-ynyl-4H-benzo[1,4]oxazin-3-one with a purity of 98.4% were dissolved in 6 g THF. 0.95 g (6.1 mmol) phenyl chloroformate were added. A temperature rise from 23° C. to 32° C. was observed. The mixture was stirred for 1 h at room temperature. The mixture was evaporated to dryness. 2.2 g of the product with a purity of 96.2% determined by quantitative HPLC method A ($t_R$=5.7 min) were obtained, which corresponds to a chemical yield 97%.

Example 1.4

6.5 g (24.9 mmol) 6-Amino-2,2,7-trifluoro-4-prop-2-ynyl-4H-benzo[1,4]oxazin-3-one with a purity of 98.1% were dissolved in 18.8 g ethyl acetate. The solution was heated to 77° C. and 4.3 g (27.5 mmol) phenyl chloroformate were added within 30 min. The mixture was stirred for 1 h at 77° C. and evaporated to dryness. 9.95 g of the product with a purity of 94.6% determined by quantitative HPLC method A ($t_R$=5.7 min) were obtained, which corresponds to a chemical yield of 100%.

Example 1.5

In a nitrogen inerted, stirred reactor 119.8 g of dry ethyl acetate (100%) and 119.8 g (0.758 mol) of phenyl chloroformate (99%) was precharged and heated up to 85° C. (reflux conditions). 868.8 g (0.702 mol) of a 20.7% solution of 6-Amino-2,2,7-trifluoro-4-prop-2-ynyl-4H-benzo[1,4]oxazin-3-one in ethyl acetate was preheated to 60° C. and dosed over 2.5 h. During the dosage HCl gas was formed as co-product and sent to a scrubber operated with NaOH (10%). After a post reaction time of 0.5 h at 79° C. (reflux conditions), 634 g of the solvent was distilled off at normal pressure. Subsequently 698 g of fresh ethyl acetate (100%) was added and 647 g distilled off again. 876.9 g of dry DMF (100%) was added and 280.8 g of solvent (mainly ethyl acetate) was distilled off at 120-10 mbar and internal temperatures up to 50° C. 1112.0 g of a DMF solution containing 23.4% of the product determined by quantitative HPLC method B ($t_R$=6.9 min) was obtained, corresponding to 98.5% chemical yield.

2. Preparation of Precursors and Intermediates for the Carbamat-Benzoxazinones of Formula (I)

Example 2.1

2-bromo-2,2-difluoro-N,N-dimethyl-acetamide

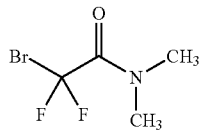

To a solution of ethyl bromodifluoroacetate (370 g, 1.82 mol) in 1000 mL of THF was added a solution of Me$_2$NH in THF (2.0 M, 1000 mL, 2.0 mol). A slightly exothermic reaction occurred. The solution was stirred at room temperature overnight. The solvent was then carefully removed by distillation and the residue purified by rectification. The product was obtained as a colorless liquid (343 g, >99% pure by GC, 1.7 mol, 93% yield).

$^1$H NMR (DMSO-d$_6$, 500 MHz): δ (ppm)=3.18 (s, 3H), 3.02 (s, 3H).

$^{13}$C NMR (DMSO-d$_6$, 125 MHz): δ (ppm)=158.6 (t, J=25 Hz); 110.5 (t, J=311 Hz); 37.3; 36.7. Boiling point: 71-76° C. (56 mbar)

Example 2.2

2-bromo-2,2-difluoro-N,N-diethyl-acetamide

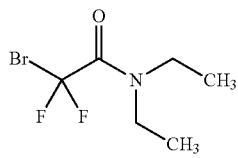

Et$_2$NH (7.9 g, 108 mmol) was added to ethyl bromodifluoroacetate (20.1 g, 99 mmol) at 30° C. The mixture was stirred for 60 min; then all volatiles were removed under reduced pressure. To the residue was added another 7.9 g of Et$_2$NH and the mixture was stirred another 60 min. Again, all volatiles were removed under reduced pressure and the residue (16.3 g, >90% purity by NMR) was used in subsequent steps without further purification.

$^1$H NMR (CDCl$_3$, 500 MHz): δ (ppm)=3.53 (q, J=7.0 Hz, 2H); 3.43 (q, J=7.0 Hz, 2H); 1.26 (t, J=7.0 Hz, 3H); 1.20 (t, J=7.0 Hz, 3H).

¹³C NMR (CDCl₃, 125 MHz): δ (ppm)=158.7 (t, J=26 Hz); 111.2 (t, J=313 Hz); 43.0; 42.1; 13.9; 11.9.

Example 2.3

2-bromo-2,2-difluoro-1-pyrrolidine-1-yl-ethanone

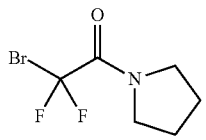 [SMILES: O=C(N1CCCC1)C(F)(F)Br]

Pyrrolidine (7.7 g, 108 mmol) was added to ethyl bromodifluoroacetate (20.2 g, 100 mmol) at 30° C. The mixture was stirred for 60 min; then all volatiles were removed under reduced pressure and the residue (24.0 g, >90% purity by NMR) was used in subsequent steps without further purification.

¹H NMR (CDCl₃, 500 MHz): δ (ppm)=3.66 (t, J=7.0 Hz, 2H); 3.58 (t, J=7.0 Hz, 2H); 2.03 (tt, J=7.0 Hz, J=7.0 Hz, 2H); 1.92 (tt, J=7.0 Hz, J=7.0 Hz, 2H).

¹³C NMR (CDCl₃, 125 MHz): δ (ppm)=158.0 (t, J=28 Hz); 111.4 (t, J=313 Hz); 48:0, 47:7, 26:5, 23:4.

Example 2.4

2-bromo-2,2-difluoro-N-isopropyl-N-methyl-acetamide

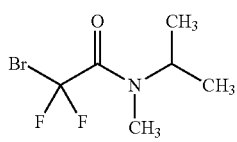

Methylisopropylamine (7.9 g, 108 mmol) was added to ethyl bromodifluoroacetate (20.0 g, 99 mmol) at 30° C. The mixture was stirred for 60 min; then all volatiles were removed under reduced pressure. The residue (10.4 g, >90% purity by NMR) was used in subsequent steps without further purification.

52:48 mixture of rotamers

¹H NMR (CDCl₃, 500 MHz): δ (ppm)=4.54-4.56 (m, 1H); 4.48-4.50 (m, 1H); 3.01 (s, 3H); 2.88 (s, 3H); 1.26 (d, J=7.0 Hz, 6H); 1.18 (d, J=7.0 Hz, 6H).

¹³C NMR (CDCl₃, 125 MHz): δ (ppm)=158.8 (t, J=26 Hz); 111.4 (t, J=313 Hz); 110.8 (t, J=313 Hz); 49.0; 47.1; 29.0; 27.6; 19.9; 18.8.

Example 2.5

2-bromo-2,2-difluoro-1-morpholine-1-yl-ethanone

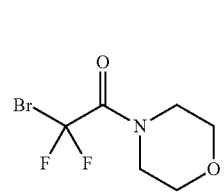

Morpholine (9.4 g, 108 mmol) was added to ethyl bromodifluoroacetate (20.0 g, 99 mmol) at 30° C. The mixture was stirred for 60 min; then all volatiles were removed under reduced pressure and the residue (13.0 g, >90% purity by NMR) was used in subsequent steps without further purification.

¹H NMR (CDCl₃, 500 MHz): δ (ppm)=3.75-3.82 (m, 4H); 3.63-3.69 (m, 4H).

¹³C NMR (CDCl₃, 125 MHz): δ (ppm)=157.1 (t, J=26 Hz); 110.2 (t, J=310 Hz); 65.7; 65.4; 46.8; 43.4.

Example 2.6

2,2-difluoro-2-(3-fluoro-phenoxy)-N,N-dimethylacetamide from 3-fluorophenol

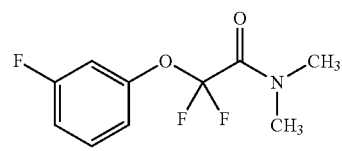 [SMILES: CN(C)C(=O)C(F)(F)Oc1cccc(F)c1]

A mixture of 3-fluoro-phenol (9.8 g, 87.4 mmol), 2-bromo-2,2-difluoro-N,N-dimethyl-acetamide (18.3 g, 89.6 mmol) and K₂CO₃ (13.3 g, 96.2 mmol) in 75 g of DMAC was heated to 100° C. for 1 h and then heated to 120° C. for 2 h. The reaction mixture was then cooled to room temperature and poured on 250 mL of H₂O and 50 mL of toluene. The aqueous phase was extracted with 25 g of toluene. The combined organic layers were extracted with 5% NaOH (20 g) and H₂O (2×20 g) and dried over Na₂SO₄. The product (18.5 g, >98% purity by quant. HPLC, 77.8 mmol, 89% yield) was obtained after removal of all volatiles under reduced pressure as a slightly yellow liquid. The material could be used in subsequent steps without further purification or purified by fractionated distillation.

¹H NMR (CDCl₃, 500 MHz): δ (ppm)=7.52-7.57 (m, 1H); 7.18-7.26 (m, 3H); 3.27 (s, 3H); 3.04 (s, 3H).

¹³C NMR (CDCl₃, 125 MHz): δ (ppm)=162.9 (d, J=245 Hz); 158.3 (t, J=35 Hz); 150.3 (d, J=11 Hz); 131.6 (d, J=9 Hz); 117.6 (d, J=3 Hz); 115.7 (t, J=271 Hz); 113.8 (d, J=21 Hz); 109.5 (d, J=25 Hz); 37.1; 36.5.

Boiling point: 102° C. (0.5 mbar)

Example 2.7

2,2-difluoro-2-(3-fluoro-phenoxy)-N,N-diethyl-acetamide from 3-fluorophenol

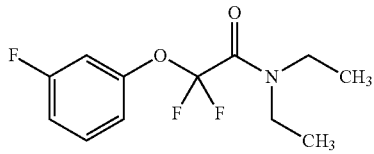 [SMILES: CCN(CC)C(=O)C(F)(F)Oc1cccc(F)c1]

To a mixture of 3-fluoro-phenol (4.9 g, 43.5 mmol), and K$_2$CO$_3$ (6.6 g, 47.8 mmol) in 43 g of DMAC at 100° C. was added 2-bromo-2,2-difluoro-N,N-diethyl-acetamide (10 g, 43.5 mmol). The mixture was kept at that temperature for 1 h and then heated to 120° C. for 2 h. The reaction mixture was then cooled to room temperature and poured on 120 mL of H$_2$O and 50 mL of toluene. The aqueous phase was extracted with 25 g of toluene. The combined organic layers were extracted with 5% NaOH (20 g) and H$_2$O (2×20 g) and dried over Na$_2$SO$_4$. The product (10.2 g, >90% purity by NMR) was obtained after removal of all volatiles under reduced pressure as a slightly yellow liquid. The material could be used in subsequent steps without further purification.

$^1$H NMR (CDCl$_3$, 500 MHz): δ (ppm)=7.31-7.36 (m, 1H); 7.02-7.05 (m, 1H); 6.95-6.99 (m, 2H); 3.58 (q, J=7.0 Hz, 2H); 3.45 (q, J=7.0 Hz, 2H); 1.26 (t, J=7.0 Hz, 3H); 1.18 (t, J=7.0 Hz, 3H).

$^{13}$C NMR (CDCl$_3$, 125 MHz): δ (ppm)=162.8 (d, J=246 Hz); 158.3 (t, J=31 Hz); 150.4 (d, J=10 Hz); 130.5 (d, J=9 Hz); 116.8 (d, J=3 Hz); 115.4 (t, J=273 Hz); 113.1 (d, J=21 Hz); 109.2 (d, J=25 Hz); 42.2; 41.5; 14.0; 12.2.

Example 2.8

2,2-difluoro-2-(3-fluoro-phenoxy)-1-pyrrolidine-1-yl-ethanone from 3-fluorophenol

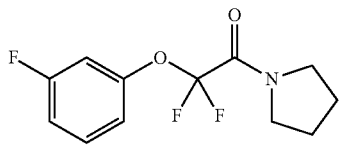 [SMILES: O=C(N1CCCC1)C(F)(F)Oc1cccc(F)c1]

To a mixture of 3-fluoro-phenol (4.5 g, 40.0 mmol), and K$_2$CO$_3$ (6.1 g, 44.0 mmol) in 40 g of DMAC at 100° C. was added 2-bromo-2,2-difluoro-1-pyrrolidine-1-yl-ethanone (9.1 g, 40.0 mmol). The mixture was kept at that temperature for 1 h and then heated to 120° C. for 2 h. The reaction mixture was then cooled to room temperature and poured on 120 mL of H$_2$O and 30 mL of toluene. The aqueous phase was extracted with 25 g of toluene. The combined organic layers were extracted with 10% NaOH (10 g) and H$_2$O (2×15 g) and dried over Na$_2$SO$_4$. The product (8.3 g, >90% purity by NMR) was obtained after removal of all volatiles under reduced pressure as a slightly yellow liquid. The material could be used in subsequent steps without further purification.

$^1$H NMR (CDCl$_3$, 500 MHz): δ (ppm)=7.32-7.36 (m, 1H); 7.02-7.06 (m, 1H); 6.95-7.00 (m, 2H); 3.76 (t, J=6.5 Hz, 2H); 3.59 (t, J=6.5 Hz, 2H); 1.98-2.03 (m, 2H); 1.88-1.94 (m, 2H).

$^{13}$C NMR (CDCl$_3$, 125 MHz): δ (ppm)=162.8 (d, J=246 Hz); 157.6 (t, J=35 Hz); 150.4 (d, J=10 Hz); 130.5 (d, J=10 Hz); 117.0 (d, J=4 Hz); 115.3 (t, J=273 Hz); 113.2 (d, J=21 Hz); 109.3 (d, J=25 Hz); 47.4; 47.0; 26.4; 23.5.

Example 2.9

2,2-difluoro-2-(3-fluoro-phenoxy)-N-isopropyl-N-methyl-acetamide from 3-fluorophenol

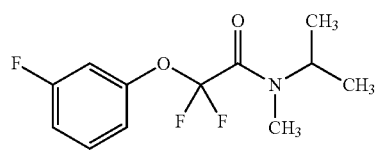 [SMILES: CC(C)N(C)C(=O)C(F)(F)Oc1cccc(F)c1]

To a mixture of 3-fluoro-phenol (4.9 g, 43.5 mmol), and K$_2$CO$_3$ (6.6 g, 47.8 mmol) in 46 mL of DMF at 100° C. was added 2-bromo-2,2-difluoro-N-isopropyl-N-methyl-acetamide (10 g, 43 mmol). The mixture was kept at that temperature for 1 h and then heated to 120° C. for 2 h. The reaction mixture was then cooled to room temperature and poured on 120 mL of H$_2$O and 30 mL of toluene. The aqueous phase was extracted with 30 mL of toluene. The combined organic layers were extracted with 10% NaOH (16 g) and H$_2$O (2×15 g) and dried over MgSO$_4$. The product (8.6 g, >90% purity by NMR) was obtained after removal of all volatiles under reduced pressure as a slightly yellow liquid. The material could be used in subsequent steps without further purification.

51:49 Mixture of Rotamers $^1$H NMR (CDCl$_3$, 500 MHz): δ (ppm)=7.31-7.36 (m, 2H); 7.02-7.05 (m, 2H); 6.94-6.99 (m, 4H); 4.79 (sept., J=7.0 Hz, 1H); 4.53 (sept., J=7.0 Hz, 1H); 3.05 (s, 3H); 2.90 (s, 3H); 1.26 (d, J=7.0 Hz, 6H); 1.16 (d, J=7.0 Hz, 6H).

$^{13}$C NMR (CDCl$_3$, 125 MHz): δ (ppm)=162.9 (d, J=246 Hz); 162.8 (d, J=246 Hz); 158.6 (t, J=35 Hz); 158.5 (t, J=35 Hz); 150.5; 150.4; 130.6 (d, J=9 Hz); 130.5 (d, J=9 Hz); 116.8 (d, J=3 Hz); 116.6 (d, J=3 Hz); 115.6 (t, J=273 Hz); 115.5 (t, J=273 Hz); 113.2 (d, J=21 Hz); 113.1 (d, J=21 Hz); 109.2 (d, J=25 Hz); 109.1 (d, J=25 Hz); 48.4; 46.4; 28.2; 27.3; 20.3; 18.9.

Example 2.10

2,2-difluoro-2-(3-fluoro-phenoxy)-1-morpholino-1-yl-ethanone from 3-fluorophenol

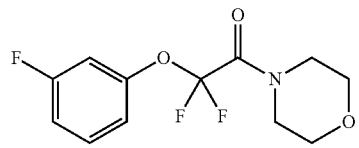 [SMILES: O=C(N1CCOCC1)C(F)(F)Oc1cccc(F)c1]

A mixture of 3-fluoro-phenol (5.6 g, 48.3 mmol), 2-bromo-2,2-difluoro-1-morpholine-1-yl-ethanone (11.7 g, 48 mmol) and K$_2$CO$_3$ (8.0 g, 57.9 mmol) in 50 g of DMAC was heated to 100° C. for 1 h and then heated to 120° C. for 2 h. The reaction mixture was then cooled to room temperature and poured on 250 mL of H$_2$O and 50 mL of toluene. The aqueous phase was extracted with 25 g of toluene. The combined organic layers were extracted with 5% NaOH (20 g) and H$_2$O (2×20 g) and dried over Na$_2$SO$_4$. The crude product was obtained after removal of all volatiles under reduced pressure as a slightly yellow liquid. The material could be used in subsequent steps without further purification.

$^1$H NMR (CDCl$_3$, 500 MHz): δ (ppm)=7.31-7.36 (m, 1H); 7.01-7.04 (m, 1H); 6.94-6.99 (m, 2H); 3.68-3.78 (m, 8H).

$^{13}$C NMR (CDCl$_3$, 125 MHz): δ (ppm)=162.9 (t, J=246 Hz); 157.6 (t, J=35 Hz); 150.3 (d, J=11 Hz); 130.7 (d, J=9 Hz); 116.7 (d, J=4 Hz); 115.3 (t, J=273 HZ); 113.3 (d, J=20 Hz); 109.0 (d, J=25 Hz); 66.7; 66.6; 46.8; 43.6.

Example 2.11

2,2-difluoro-2-(5-fluoro-2-nitro-phenoxy)-N,N-dimethyl-acetamide

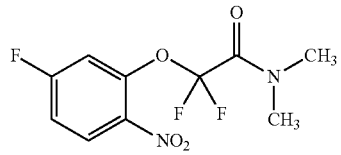 [SMILES: CN(C)C(=O)C(F)(F)Oc1cc(F)ccc1[N+](=O)[O-]]

A mixture of 2-nitro-5-fluoro-phenol (3.0 g, 19.1 mmol), 2-bromo-2,2-difluoro-N,N-dimethyl-acetamide (3.9 g, 19.1 mmol) and Na$_2$CO$_3$ (2.1 g, 19.8 mmol) in 30 mL of DMAC was heated to 100° C. overnight. The mixture was then poured on 50 mL of H$_2$O and extracted with TBME (2×50 mL). The combined organic layers were washed with 10% NaOH (50 mL) and dried over Na$_2$SO$_4$. The crude product was obtained after evaporation of all volatiles. Purification by chromatography on silica gave the product (1.8 g, 6.4 mmol, 38% yield) as a yellow oil that solidified upon standing.

$^1$H NMR (CDCl$_3$, 500 MHz): δ (ppm)=8.04 (dd, J=5.5 Hz, J=9.0 Hz, 1H); 7.26-7.29 (m, 1H); 7.13 (dd, J=2.5 Hz, J=7.5 Hz, 1H); 3.25 (s, 3H); 3.09 (s, 3H).

$^{13}$C NMR (CDCl$_3$, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

Example 2.12

2,2-difluoro-2-(5-fluoro-4-nitro-phenoxy)-N,N-dimethyl-acetamide

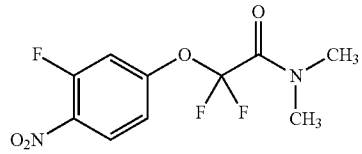 [SMILES: CN(C)C(=O)C(F)(F)Oc1ccc([N+](=O)[O-])c(F)c1]

Nitric acid (100%, 200 mL, 4.8 mol) was cooled to −5° C. 2,2-Difluoro-2-(3-fluoro-phenoxy)-N,N-dimethyl-acetamide (19.0 g, 81.5 mmol) was added at rate to keep the temperature below −2° C. Upon complete addition stirring was continued for 30 min. The reaction mixture was then poured on 450 mg ice-water. The aqueous phase was extracted with TBME (3×100 mL); the combined organic phases were washed with water (100 mL) and brine (100 mL) and dried over MgSO$_4$. Evaporation of the solvent gave the crude product that was purified by preparative HPLC. The product (6.5 g, >98% by HPLC, 28% yield) was obtained as a yellow solid.

$^1$H NMR (DMSO-d$_6$, 500 MHz): δ (ppm)=8.31 (t, J=9.0 Hz, 1H); 7.68 (dd, J=2.5 Hz, J=12.0 Hz, 1H); 7.38-7.41 (m, 1H); 3.21 (s, 3H), 3.00 (m, 3H).

Example 2.13

2,2-difluoro-2-(2,4-dinitro-5-fluoro-phenoxy)-N,N-dimethyl-acetamide

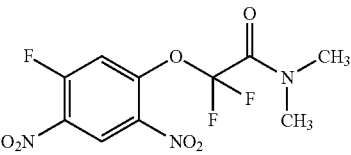 [SMILES: CN(C)C(=O)C(F)(F)Oc1cc(F)c([N+](=O)[O-])cc1[N+](=O)[O-]]

To a mixture of H$_2$SO$_4$ (98%, 34.5 g, 345 mmol) and HNO$_3$ (100%, 11.0 g, 175 mmol) at room temperature was added 2,2-difluoro-2-(3-fluoro-phenoxy)-N,N-dimethyl-acetamide (8.7 g, 37 mmol). The temperature rose to 40° C. and was kept at that temperature for further 3 h. The mixture was then poured on 100 g of ice-water. The precipitate was taken up in 50 g of toluene and the aqueous phase was extracted with 25 g of toluene. The combined org. phases were washed with saturated NaHCO$_3$ solution and water. The crude product (11.5 g, 82% purity by quant. HPLC, 29 mmol, 78% yield) was obtained after removal of all volatiles as a yellowish solid. Analytically pure material the crude material could be obtained after recrystallisation from cyclohexane/EtOAc (80:20).

$^1$H NMR (CDCl$_3$, 400 MHz): δ (ppm)=8.82 (d, J=7.5 Hz, 1H); 7.52 (d, J=11.0 Hz, 1H); 3.26 (s, 3H); 3.11 (s, 3H).

$^{13}$C NMR (CDCl$_3$, 100 MHz): δ (ppm)=157.1 (d, J=276 Hz); 156.7 (d, J=34 Hz); 147.6 (td, J=3 Hz, J=11 Hz); 136.9; 132.9 (d, J=9 Hz); 124.2; 115.3 (t, J=281 Hz); 111.7 (td, J=3 Hz, J=26 Hz); 36.8; 36.7.

Melting point: 66° C.

Example 2.14

2,2-difluoro-2-(2,4-dinitro-5-fluoro-phenoxy)-N,N-diethyl-acetamide

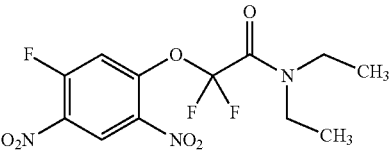

To a mixture of H$_2$SO$_4$ (98%, 261 g, 2.61 mol) and HNO$_3$ (100%, 107 g, 1.7 mol) at 0° C. was added 2,2-difluoro-2-(3-fluoro-phenoxy)-N,N-diethyl-acetamide (34 g, 130 mmol) with cooling. The mixture was then warmed to r.t. and stirred for further 3 h. Then, the mixture was poured on 750 g ice-water. TBME (250 mL) was added and the aqueous phase was extracted with TBME (200 mL). The combined organic phases were washed with water (300 mL), saturated NaHCO$_3$ solution and brine. Drying over Na$_2$SO$_4$ and evaporation of all volatiles gave the product as a yellow solid.

$^1$H NMR (CDCl$_3$, 500 MHz): δ (ppm)=8.82 (d, J=7.5 Hz); 7.53 (d, J=11.0 Hz, 1H); 3.57 (q, J=7.0 Hz, 2H); 3.45 (q, J=7.0 Hz, 2H); 1.27 (t, J=7.0 Hz, 3H); 1.18 (t, J=7.0 Hz, 3H).

$^{13}$C NMR (CDCl$_3$, 125 MHz): δ (ppm)=157.6 (d, J=268 Hz); 156.6 (t, J=34 Hz); 148.2 (d, J=11 Hz); 137.3; 133.3 (d, J=8 Hz); 124.7; 115.8 (t, J=281 Hz); 112.3 (d, J=26 Hz); 42.3; 42.0; 14.1; 12.2.

Example 2.15

2,2-difluoro-2-(2,4-dinitro-5-fluoro-phenoxy)-1-pyrrolidine-1-yl-ethanone

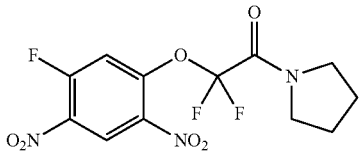 [SMILES: O=C(N1CCCC1)C(F)(F)Oc1cc(F)c([N+](=O)[O-])cc1[N+](=O)[O-]]

To a mixture of H$_2$SO$_4$ (98%, 22.0 g, 220 mmol) and HNO$_3$ (100%, 8.5 g, 135 mmol) at 0° C. was added 2,2-difluoro-2-(3-fluoro-phenoxy)-1-pyrrolidine-1-yl-ethanone (3.3 g, 12.7 mmol). The temperature rose to 10° C. and was kept at that temperature for further 16 h. The mixture was then poured on 150 g of ice-water and 80 mL of TBME. The aqueous phase was extracted with 50 mL of TBME. The combined org. phases were washed with saturated NaHCO$_3$ solution and water. The crude product (3.6 g, >98% purity by HPLC, 10.3 mmol, 81% yield) was obtained after removal of all volatiles as a yellow solid.

$^1$H NMR (CDCl$_3$, 500 MHz): δ (ppm)=8.81 (d, J=7.5 Hz, 1H); 7.54 (d, J=11.0 Hz, 1H); 3.72-3.78 (m, 4H); 3.54-3.59 (m, 4H); 2.02-2.09 (m, 4H); 1.92-1.98 (m, 4H).

$^{13}$C NMR (CDCl$_3$, 125 MHz): δ (ppm)=157.6 (d, J=274 Hz); 155.7 (t, J=34 Hz); 148.2 (d, J=11 Hz); 137.4; 133.3 (d, J=8 Hz); 124.7; 115.6 (t, J=280 Hz); 112.5 (d, J=32 Hz); 47.9; 47.0; 26.4; 23.5.

Melting point: 78° C.

Example 2.16

2,2-difluoro-2-(2,4-dinitro-5-fluoro-phenoxy)-1-morpholine-1-yl-ethanone

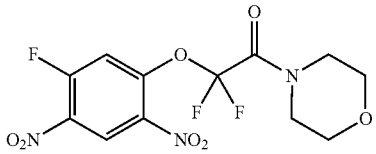

To a mixture of H$_2$SO$_4$ (96%, 68.8 g, 701 mmol) and HNO$_3$ (100%, 13.3 g, 210 mmol) at 0° C. was added 2,2-difluoro-2-(3-fluoro-phenoxy)-1-morpholine-1-yl-ethanone (18.3 g, 90% pure, 60 mmol). The temperature was eventually increased to 40° C. and was kept at room temperature for 60 min. The mixture was then poured on 160 g of ice-water. and 80 g of chlorobenzene. The aqueous phase was extracted with chlorobenzene (2×40 mL). The combined org. phases were washed with saturated NaHCO$_3$ solution and water. The crude product (12.3 g, >90% purity by HPLC) was obtained after removal of all volatiles as a reddish solid. Recrystallisation from n-BuOH (150 mL) gave the product as a yellow solid.

$^1$H NMR (CDCl$_3$, 500 MHz): δ (ppm)=8.82 (d, J=7.0 Hz, 1H); 7.52 (d, J=10.5 Hz, 1H); 3.68-3.78 (m, 8H).

$^{13}$C NMR (CDCl$_3$, 125 MHz): δ (ppm)=157.5 (d, J=274 Hz); 155.8 (t, J=34 Hz); 147.6 (d, J=11 Hz); 137.2; 135.3; 124.7; 115.4 (t, J=281 Hz); 112.1 (d, J=26 Hz); 66.5; 66.4; 46.6; 43.8. Melting point: 96° C.

Example 2.17

2,2-difluoro-2-(2,4-diamino-5-fluoro-phenoxy)-N,N-dimethyl-acetamide

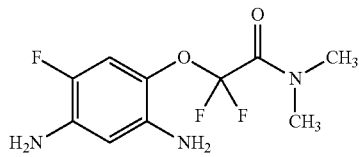 [SMILES: CN(C)C(=O)C(F)(F)Oc1cc(F)c(N)cc1N]

To a solution of 2,2-difluoro-2-(2,4-dinitro-5-fluoro-phenoxy)-N,N-dimethyl-acetamide (22.0 g, 68.1 mmol) in toluene (200 g) was added and Pd/C (10% Pd, dry catalyst, 0.7 g, 0.7 mmol). Thereafter, MeOH (80 g) was added and the mixture stirred under an atmosphere of hydrogen (pressure of 0.1 bar) at 45° C. for 90 min. After completion of the reaction the pressure was released, the catalyst was filtered off and the filtrate was evaporated to dryness. The product (17.3 g, 84% pure by NMR, 55.2 mmol, 81% yield) was obtained as an off-white solid. If desired, the purity can be increased by chromatography (SiO$_2$, cyclohexane/EtOAc mixtures).

$^1$H NMR (DMSO-d$_6$, 500 MHz): δ (ppm)=6.79 (d, J=11.0 Hz, 1H); 6.16 (d, J=8.5 Hz, 1H); 4.95 (bs, 2H); 4.60 (bs, 2H); 3.19 (s, 3H); 2.96 (bs, 3H).

$^{13}$C NMR (DMSO-d$_6$, 125 MHz): δ (ppm)=158.3 (t, J=35 Hz); 141.7 (d, J=278 Hz); 137.6; 134.9 (d, J=14 Hz); 123.9 (d, J=9 Hz); 115.8 (t, J=272 Hz); 109.2 (d, J=22 Hz); 102.0 (d, J=4 Hz); 36.9; 36.2.

Example 2.18

2,2-difluoro-2-(2,4-diamino-5-fluoro-phenoxy)-N,N-diethyl-acetamide

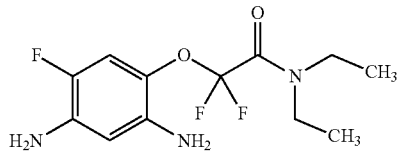

A solution of 2,2-difluoro-2-(2,4-dinitro-5-fluoro-phenoxy)-N,N-diethyl-acetamide (13.5 g, 38.4 mmol) and Pd/C (10% Pd, dry catalyst, 2.0 g, 1.9 mmol) in MeOH (395) was stirred under an atmosphere of hydrogen (pressure of 0.1 bar)

at 50° C. for 2 h. After completion of the reaction the pressure was released, the catalyst was filtered off and the filtrate was evaporated to dryness. The product was purified by column chromatography (SiO₂, cyclohexane/EtOAc mixtures). The product was obtained as an off-white solid (11.0 g, 88% pure by NMR, 33.2 mmol, 86% yield).

$^1$H NMR (CDCl₃, 500 MHz): δ (ppm)=6.85 (d, J=11.0 Hz, 1H); 6.19 (d, J=8.5 Hz, 1H); 3.71 (bs, 4H); 3.58 (q, J=7.0 Hz, 2H); 3.45 (q, J=7.0 Hz, 2H); 1.25 (t, J=7.0 Hz, 3H); 1.19 (t, J=7.0 Hz, 3H).

$^{13}$C NMR (CDCl₃, 125 MHz): δ (ppm)=158.8 (t, J=35 Hz); 143.7 (d, J=231 Hz); 136.5; 133.5 (d, J=14 Hz); 126.9 (d, J=9 Hz); 116.1 (t, J=273 Hz); 110.3 (d, J=23 Hz); 103.8 (d, J=3 Hz); 42.4; 41.6; 14.1; 12.6.

Example 2.19

6-amino-2,2,7-trifluoro-4H-benzo-[1,4]oxazin-3-one from 2,2-difluoro-2(2,4-dinitro-5-fluoro-phenoxy)]-N,N-dimethyl-acetamide

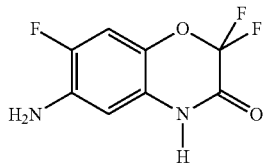 [SMILES: Nc1cc2c(cc1F)OC(F)(F)C(=O)N2]

To a solution of 2,2-difluoro-2-(2,4-dinitro-5-fluoro-phenoxy)-N,N-dimethyl-acetamide (60.0 g, 186 mmol) in toluene (432 g) was added Pd on charcoal (5% Pd, 50% water content, 1.1 mmol). Thereafter MeOH (492 g) was added and the mixture was stirred under an atmosphere of hydrogen (over pressure 0.1 bar) at 45° C. for 2 h. After completion of the reaction the pressure was released, concentrated HCl (36.5%, 22 g, 220 mmol) added and the reaction mixture heated to reflux for further 1 h. The catalyst was filtered off, the pH adjusted with NaOH to 9 and the MeOH distilled off under reduced pressure. After addition of water (200 g) and stirring for 1 h the precipitate was filtered off, washed twice with water (100 g) and dried at 50° C. under reduced pressure. The product was obtained as a tan solid (38.9 g, 90% pure by NMR, 160 mmol, 86% yield).

$^1$H NMR (DMSO-d₆, 500 MHz): δ (ppm)=11.9 (bs, 1H); 7.15 (d, J=11.0 Hz, 1H); 6.55 (d, J=8.5 Hz, 1H); 5.28 (bs, 2H).

$^{13}$C NMR (DMSO-d₆, 125 MHz): δ (ppm)=153.7 (t, J=38 Hz); 146.1 (d, J=235 Hz); 133.9 (d, J=15 Hz); 127.3 (d, J=11 Hz); 120.9 (d, J=3 Hz); 113.1 (t, J=260 Hz); 104.9 (d, J=24 Hz); 102.4 (d, J=5 Hz).

Examples 2.20 to 2.24

6-Amino-2,2,7-trifluoro-4-prop-2-ynyl-4H-benzo[1,4]oxazin-3-one

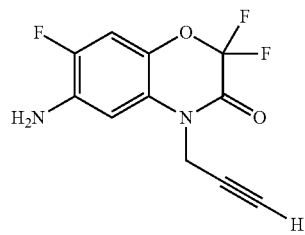 [SMILES: C#CCN1C(=O)C(F)(F)Oc2cc(F)c(N)cc21]

Example 2.20

61.0 g (0.2678 mol) 6-amino-2,2,7-trifluoro-4H-benzo[1,4]oxazin-3-one, 360 g ethyl acetate and 38.9 g (0.2815 mol) potassium carbonate were initially charged at 25° C. in a stirred vessel. 43.8 g (0.2945 mol) propargyl bromide (80% w/w in toluene) were added at 25-30° C. within 15 minutes. Thereafter the reaction mixture was stirred at 78° C. for 8 hours and then cooled to 25° C. The precipitated salt was filtered off and washed with 360 g of ethyl acetate. The combined ethyl acetate solutions were washed with 200 g hydrochloric acid (1%) and twice with 200 g water. The organic phase was dried by azeotropic distillation (ca. 600 g distillate). The remaining solution (158.5 g) comprised 40.3% by weight of the desired product (HPLC analysis with external standard). The yield (based on the amino compound used) was 93.1%.

From a small quantity of the solution the solvent was completely distilled off at reduced pressure. The remaining residue was recrystallized from methanol and dried. The obtained crystals (melting point: 239.2° C.) showed the following spectroscopical data:

1H-NMR (500 MHz, DMSO-d6): δ (ppm)=3.45 (s, 1H), 4.74 (s, 2H), 5.42 (s, 2H), 6.85 (d, 1H), 7.26 (d, 1H).

Example 2.21

219.1 g (1.0 mol) 6-amino-2,2,7-trifluoro-4H-benzo[1,4]oxazin-3-one, 1100 g dimethylformamide and 145.5 g (1,053 mol) potassium carbonate were initially charged at 25° C. in a stirred vessel. 163.2 g (1.1 mol) propargyl bromide (80% w/w in toluene) were added at 25-30° C. within 30 minutes. Thereafter the reaction mixture was stirred at 60° C. for 2 hours and then cooled to 25° C. The precipitated salt was filtered off and washed with 3300 g of ethyl acetate. The combined organic solutions were washed with 750 g water and with 750 g sodium sulfate solution (5%). The combined inorganic phases were extracted three times with 550 g ethyl acetate. All organic phases were combined and dried by azeotropic distillation. The remaining solution (635.3 g) comprised 40.05% by weight of the desired product (HPLC analysis with external standard). The yield (based on the amino compound used) was 97.8%.

Example 2.22

0.8 g (0.00348 mol) 6-amino-2,2,7-trifluoro-4H-benzo[1,4]oxazin-3-one (purity: 94.9%) were dissolved in 19.76 g ethyl acetate at 20° C. 0.075 g ethyltrimethylammoniumiodide and 0.284 g (0.00205 mol) potassium carbonate were added. Then 0.463 g (0.00435 mol) propargyl chloride (70% in toluene) were added. The mixture was heated to reflux (73-77° C.) over 10 h. Reaction mixture was cooled to 25° C. and 20 g water was added under stirring. Phases were separated. The organic phase was evaporated to dryness at 45° C./4 mbar. 0.9 g solid with a purity of 95.0% (determined by quantitative HPLC) were isolated (yield: 95.9%).

Example 2.23

0.8 g (0.00348 mol) 6-amino-2,2,7-trifluoro-4H-benzo[1,4]oxazin-3-one (purity: 94.9%) were dissolved in 20 g ethyl acetate at 20° C. 0.505 g (0.00365 mol) potassium carbonate and 0.614 g (0.00435 mol) propargyl mesylate (95%) were added as solid. The mixture was heated to reflux (77° C.) over 3 h. Reaction mixture was cooled to 25° C. and 20 g water was added under stirring. Phases were separated. The organic phase was evaporated to dryness at 45° C./4 mbar. 1.0 g solid with a purity of 88.1% (determined by quantitative HPLC) were isolated (yield: 98.9%).

Example 2.24

13.22 g (0.06 mol) 6-amino-2,2,7-trifluoro-4H-benzo[1,4]oxazin-3-one (purity: 99%) were dissolved in 48 g DMF at 20° C. 10.67 g (0.077 mol) potassium carbonate and 7.98 g (0.075 mol) propargyl chloride (70% in toluene) were added. The mixture was stirred at 72° C. for 2 h. Reaction mixture was cooled to 3° C. and 120 g water were added under stirring over a period of 2 h at 3-5° C. Suspension was stirred for 3 h at 0-5° C. The solid was filtered off and washed with water. The wet solid was dried in a vacuum cabinet at 50° C./3 mbar over 17 hours. 14.8 g of a light brown solid with a purity of 99.3% (determined by quant. HPLC) were isolated (yield: 95.6%).

3. Preparation of Carbamates of Formula (IX)

Example 3.1

Methyl N-methyl-N-(methylcarbamothioyl)carbamate

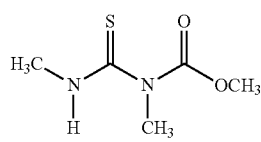

420.9 g (4.00 mol) N,N-dimethylthiourea with a purity of 99% were charged to 2000 g toluene. 507 g (4.78 mol) sodium carbonate was added and the suspension heated to 65° C. Afterwards 432.2 g (4.60 mol) methyl chloroformate were dosed in over 5 h at 65° C. The mixture was poststirred at the same temperature over 0.5 h. For work up, demineralized water was added under agitation and the phases separated. The aqueous phase was extracted with 800 g toluene and the organic phases were combined. The product content of the organic solution was determined with 15.15% by quant. HPLC (HPLC-method A; $t_R$=3.6 min), which corresponds to a chemical yield of 90.3%.

$^1$H-NMR (CDCl$_3$, 400 MHz): 10.1-10.3 (1H, s), 3.82 (3H, s), 3.66 (3H, s), 3.17 (3H, d).

Examples 3.2 and 3.3

Phenyl N-methyl-N-(methylcarbamothioyl)carbamate

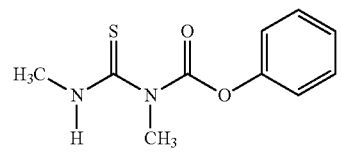

Example 3.2

50.0 g (0.66 mol) methylisothiocyanate with a purity of 97% were added to xylene (isomeric mixture). 20.6 g (0.66 mol) of methyl amine were introduced at 20-30° C. with a dip tube resulting in the formation of two layers. The lower slightly yellow layer was separated, transferred to a rotary evaporator, and treated with a vacuum of 10 mbar at 50° C. for 30 min. Qualitative analytics (HPLC, GC) showed complete conversion to N,N'-dimethyl thiourea (no MITC detectable), the composition was 88% DMTU and 12% xylene (GC-area-%).

The N,N'-dimethyl thiourea (0.66 mol) obtained was dissolved in ethyl acetate. 106.0 g (1.00 mol) sodium carbonate were added and 156.6 g (1.00 mol) phenyl chloroformate were dosed over a period of 30 min with the temperature rising to 63° C. The mixture was poststirred at 66° C. for 0.5 h. Demineralized water was added under agitation at the same temperature and the phases separated. A vacuum was applied to the organic phase and 200 ml of a two-phase liquid were distilled off. The vessel was cooled to 5° C. and stirred for 1 h at this temperature. The product was collected by filtration and washed once with cyclohexane. The resulting solid was dried to yield 114.0 g (0.50 mol) of colourless crystals with a purity of 98% (HPLC-method B; $t_R$=5.93 min) and a melting point of 133-135° C. (corresponding chemical yield: 75%).

$^1$H-NMR (CDCl$_3$, 400 MHz): 10.5-10.6 (1H, s), 7.38-7.46 (2H, m), 7.24-7.32 (1H, m), 7.09-7.17 (2H, m), 3.89 (3H, s), 3.17 (3H, d).

Example 3.3

50.0 g (0.66 mol) methylisothiocyanate with a purity of 98% were added to ethyl acetate. 22.0 g (0.71 mol) of methyl amine were introduced at 20-30° C. with a dip tube. Nitrogen was bubbled through the solution for 14 h. 106.0 g (1.00 mol) sodium carbonate were added and 156.6 g (1.00 mol) phenyl chloroformate were dosed over a period of 30 min with the temperature rising from 30° C. to 60° C. The mixture was poststirred at 70° C. for 0.5 h. Demineralized water was added under agitation at the same temperature and the phases separated. A vacuum was applied to the organic phase and 100 ml of a two-phase liquid were distilled off. The vessel was cooled to 5° C. and stirred for 1 h at this temperature. The product was collected by filtration and washed once with 50 g of cyclohexane. The resulting solid was dried to yield 124.0 g (0.54 mol) of colourless crystals with a purity of 98% (HPLC-method B; $t_R$=5.93 min; corresponding chemical yield: 82.1%).

4. Preparation of the Benzoxazinones of Formula (X)

Examples 4.1 to 4.7

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

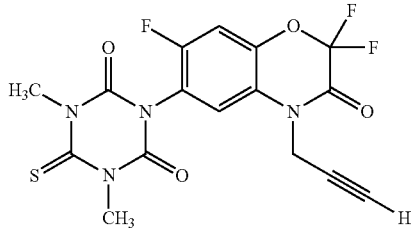 [SMILES: C#CCN1C(=O)C(F)(F)Oc2cc(F)c(-n3c(=O)n(C)c(=S)n(C)c3=O)cc21]

Example 4.1

4.49 g (20.0 mmol) phenyl N-methyl-N-(methylcarbamothioyl)carbamate and 7.84 g (20.0 mmol) phenyl N-[2,2,7-trifluoro-3-oxo-4-(prop-2-ynyl)-3,4-dihydro-2H-benzo[b][1,4]oxazin-6-yl]carbamate (purity 96%) were dissolved in 40 mL N,N-dimethylformamide (DMF), 0.33 g (4.0 mmol) sodium acetate were added and the mixture heated to 60° C. After 3.5 h 32 ml DMF were removed by distillation at 50° C. under reduced pressure. The product precipitated after addition of a mixture of 25 mL methanol and 25 mL $H_2O$. The solids were collected and washed with 10 mL water and 10 mL methanol. 7.8 g (purity by quant. HPLC 97.8 wt % corresponding to 93% chemical yield; HPLC-method A; $t_R$=5.9 min) of the title compound were obtained.

$^1$H-NMR (CDCl$_3$, 400 MHz): 7.27 (1H, d), 7.18 (1H, d), 4.76 (2H, s), 3.80 (6H, s), 2.38 (1H, s)

Example 4.2

0.56 g (2.5 mmol) phenyl N-methyl-N-(methylcarbamothioyl)carbamate and 0.98 g (2.5 mmol) phenyl N-[2,2,7-trifluoro-3-oxo-4-(prop-2-ynyl)-3,4-dihydro-2H-benzo[b][1,4]oxazin-6-yl]carbamate (purity 96%) were dissolved in 20 mL tetrahydrofuran (THF). 49 mg (0.50 mmol) potassium acetate were added and the mixture heated to 60° C. After 4 h the solvent was removed. The product solidified after addition of 10 g 60% aqueous methanol. The solids were collected and washed twice with 2 mL 60% aqueous methanol. 0.95 g (purity by quant. HPLC 99.5 wt % corresponding to 92% chemical yield; HPLC-method A; $t_R$=5.9 min) of the title compound were obtained.

Example 4.3

1.03 g (4.02 mmol) 6-amino-2,2,7-trifluoro-4-(prop-2-ynyl)-3,4-dihydro-2H-benzo[b][1,4]oxazin-3-one was dissolved in 20 mL THF. A solution of 0.63 g (4.02 mmol) phenyl chloroformate in THF was added at 55° C. The mixture was stirred for 30 min at this temperature. Formed HCl was stripped by a nitrogen stream. 8 mL DMF were added and THF distilled off under vacuum. 65 mg (0.79 mmol) sodium acetate and 0.97 g (4.02 mmol) phenyl N-methyl-N-(methylcarbamothioyl)carbamate (purity 93%) was added and the mixture stirred at 45° C. until HPLC showed complete conversion. 6 g DMF was removed by distillation under reduced pressure and the product precipitated after addition of 8 g 60% aqueous methanol. The solids were collected, washed twice with 60% aqueous methanol and dried in vacuum. 1.51 g (purity by quant. HPLC 97.3% corresponding to 97% chemical yield; HPLC-method A; $t_R$=5.9 min) of the title compound were obtained.

Example 4.4

3.24 g (20.0 mmol) methyl N-methyl-N-(methylcarbamothioyl)carbamate were dissolved in 30 g DMF and 0.21 g (2.0 mmol) Na$_2$CO$_3$ was added. The pressure was reduced to 12 mbar and the mixture heated to reflux (40-42° C.). 7.96 g (20.0 mmol) phenyl N-[2,2,7-trifluoro-3-oxo-4-(prop-2-ynyl)-3,4-dihydro-2H-benzo[b][1,4]oxazin-6-yl]carbamate (purity 94.5%) in 20 g DMF were added continuously over 60 min. Methanol formed in the course of the reaction was removed by co-distillation with DMF. The solvent volume was kept constant by addition of pure DMF from a second feed vessel. The mixture was stirred for another 30 min at this temperature and for 90 min at 25° C. The resulting solution (39.5 g) contained 20.2 wt % of the title compound corresponding to 96.5% chemical yield (HPLC-method A; $t_R$=5.9 min)

Example 4.5

In a nitrogen inerted, stirred reactor 118.7 g of dry ethyl acetate (100%) and 59.3 g (0.375 mol) of phenylchloroformate (99%) were precharged and heated up to 85° C. (reflux conditions). A solution of 100 g (0.354 mol) of 6-amino-2,2,7-trifluoro-4-(prop-2-ynyl)-3,4-dihydro-2H-benzo[b][1,4]oxazin-3-one (90.7%) in 400 g of ethyl acetate was preheated to 60° C. and dosed over 2.5 h. During the dosage HCl gas was formed as co-product and sent to a scrubber operated with NaOH (10%). After a post reaction time of 0.5 h at 79° C. (reflux conditions), 400 g of the solvent was distilled off at normal pressure. Subsequently 400 g of fresh ethyl acetate was added and distilled off again. 441.4 g of DMF was added and 162.8 g of solvent (mainly ethyl acetate) was distilled off at 120-10 mbar and internal temperatures up to 50° C. At 50° C. 80.1 g (0.350 mol) of phenyl N-methyl-N-(methylcarbamothioyl)carbamate (98.1%) was added followed by 5.8 g (0.071 mol) of dry sodium acetate (100%). The mixture was stirred 3.5 h at 50° C. Afterwards 258.0 g of DMF was distilled off at 5-10 mbar and internal temperatures up to 55° C. For precipitation of the title compound 601.8 g of a mixture methanol/water 3:2 was precharged in a second reactor and heated up to 50° C.

At 50° C. 1.8 g (0.0044 mol) of 1,5-dimethyl-6-thioxo-3-[2,2,7-trifluoro-3-oxo-4-(prop-2-ynyl)-3,4-dihydro-2H-benzo[b][1,4]oxazin-6-yl]-1,3,5-triazinane-2,4-dione was added. Then the concentrated DMF solution of the raw product was dosed in 1.5 h at 50° C. Afterwards the mixture was cooled down to 10° C. and stirred 0.5 h at 10° C. The precipitated product was isolated by filtration and washed twice with 150 g of a mixture methanol/water 3:2 precooled to 0° C. The wet filter cake was dried in a vacuum drying oven. 134.9 g (0.315 mol) of the title compound (96.3 wt % purity determined by quant. HPLC (HPLC-method B; $t_R$=7.1 min) were obtained (corresponding to 89% chemical yield).

Example 4.6

44 g (0.27 mol) methyl N-methyl-N-(methylcarbamothioyl)carbamate, purity 94.1%, in 414 g DMF were charged to a laboratory glass vessel. 4.64 g (44 mmol) $Na_2CO_3$ was added. The mixture was heated to reflux at 10 mbar/40° C. Afterwards 111 g (0.27 mol) phenyl N-[2,2,7-trifluoro-3-oxo-4-(prop-2-ynyl)-3,4-dihydro-2H-benzo[b][1,4]oxazin-6-yl]carbamate (purity 91.6%) in 372 g DMF was dosed in at 40° C. under reflux of DMF over 4 h (40° C., 10 mbar). The generated methanol was not condensed together with the DMF and so removed from the mixture. After poststirring of 30 min, the major part of DMF was distilled off (10-20 mbar, 50° C.). The vessel content was cooled to 20° C. and a mixture of 487 g MeOH and 487 g demineralized water was added for precipitation. The resulting suspension was cooled to 3° C. and the product was filtered, washed with water and dried in a vacuum cabinet at 50° C. 107 g (0.255 mol) of the product with a purity of 98.4% determined by quant. HPLC (HPLC-method A; $t_R$=5.9 min) have been obtained (corresponding to 94.5% chemical yield).

Example 4.7

0.38 g (2.0 mmol) ethyl N-methyl-N-(methylcarbamothioyl)carbamate with a purity of 91.9% was added to 3.5 g DMF. Under agitation, 0.76 g (2.0 mmol) phenyl N-[2,2,7-trifluoro-3-oxo-4-(prop-2-ynyl)-3,4-dihydro-2H-benzo[b][1,4]oxazin-6-yl]carbamate (98.5% purity) and 0.01 g (0.14 mmol) of NaOH powder were added at 35° C. After a poststirring period of 2 h, a chemical yield 70.1% was determined by quantitative HPLC analytics (HPLC-method A; $t_R$=5.9 min) of the product solution.

Example 4.8

1,5-dimethyl-6-thioxo-3-(2,2,7-trifluoro-3-oxo-3,4-dihydro-2H-benzo[b][1,4]oxazin-6-yl]-1,3,5-triazinane-2,4-dione

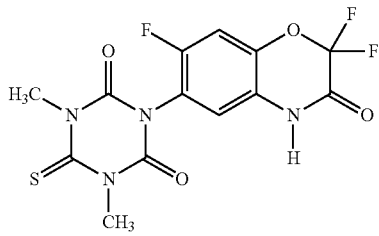

0.97 g (5.0 mmol) methyl N-methyl-N-(methylcarbamothioyl)carbamate with a purity of 83.3% was dissolved in 4.2 g DMF. 0.14 g (1.7 mmol) sodium acetate was added. The mixture was stirred at 60° C. at a pressure of 25 mbar. Via syringe a solution of 1.32 g (3.7 mmol) phenyl N-(2,2,7-trifluoro-3-oxo-3,4-dihydro-2H-benzo[b][1,4]oxazin-6-yl)carbamate (purity 95.7%) in 4.2 g DMF was added within 2 h. From time to time fresh DMF was added to maintain the solvent volume. After a poststirring period of 1 h, a chemical yield 73% was determined by quantitative HPLC analytics (HPLC-method A; $t_R$=4.9 min) of the product solution.

$^1$H-NMR (DMSO-$d_6$, 400 MHz): 11.98 (1H, br), 10.07 (1H, br), 7.54 (1H, d), 7.40-7.49 (3H, m), 7.20-7.30 (3H, m).

The invention claimed is:
1. A process for the preparation of a compound of formula (I),

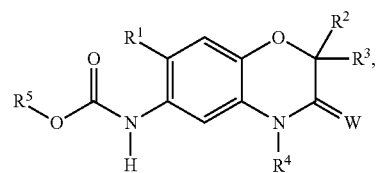

comprising reacting a compound of formula (II),

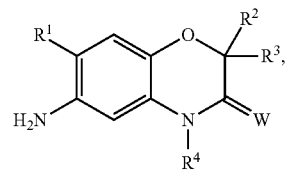

wherein
$R^1$ is H or halogen;
$R^2$ is halogen;
$R^3$ is H or halogen;
$R^4$ is H, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and
W is O or S;
with a compound of formula (III)

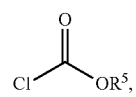

wherein
$R^5$ is phenyl, which is unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl.

2. A process as claimed in claim 1, wherein the process is carried out in the absence of a base.

3. A process as claimed in claim 1, wherein the compound of formula (II) is prepared by
a) reacting a compound of formula (VI-1)

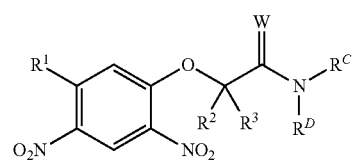

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-

$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;
with a reducing agent to give a compound of formula (V)

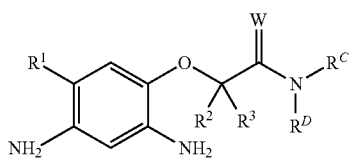
(V)

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;
b) treating the compound of formula (V) with an acid to obtain a compound of formula (II-1)

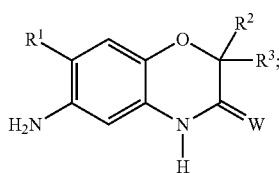
(II-1)

c) optionally reacting the compound of formula (II-1) with a base and a compound of formula (IV), $R^\# L^\#$ (IV), wherein
$R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$L^\#$ is halogen or $OS(O)_2 R^9$; and
$R^9$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy;
to give a compound of formula (II-2)

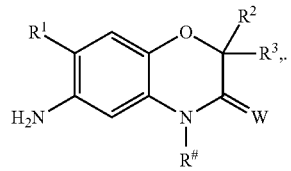
(II-2)

4. A process as claimed in claim 3, wherein the compound of formula (VI-1) is prepared by
a) reacting a compound of formula (VII)

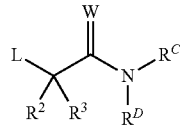
(VII)

wherein L is halogen;
with a compound of formula (VIII)

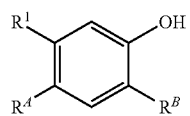
(VIII)

wherein $R^A$, $R^B$ are independently H or $NO_2$;
in the presence of a base to obtain a compound of formula (VI);

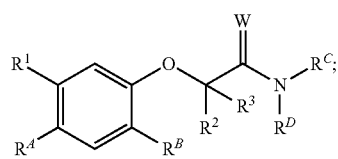
(VI)

b) and, if $R^A$ and/or $R^B$ in formula (VI) are H, reacting the compound of formula (VI) with $HNO_3/H_2SO_4$ to obtain a compound of formula (VI-1).

5. A compound of formula (I.a.a),

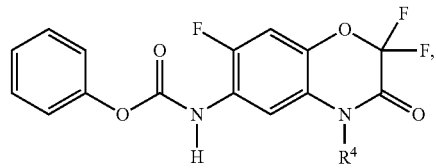
(I.a.a)

wherein
$R^4$ is H or $C_3$-$C_6$-alkynyl.
6. The compound of claim 5, wherein $R^4$ is H or propargyl.
7. The compound of claim 5, wherein $R^4$ is H.

8. The compound of claim 5, wherein $R^4$ is $C_3$-$C_6$-alkynyl.
9. The compound of claim 5, wherein $R^4$ is propargyl.

* * * * *